（12）United States Patent
Albrecht et al.

(10) Patent No.: US 7,909,760 B2
(45) Date of Patent: Mar. 22, 2011

(54) SPLIT HOOP WOUND RETRACTOR WITH GEL PAD

(75) Inventors: Jeremy J. Albrecht, Ladera Ranch, CA (US); Jennifer T. Ko, Rancho Santa Margarita, CA (US); Gary M. Johnson, Mission Viejo, CA (US); John R Brustad, Dana Point, CA (US); Donald L. Gadberry, San Clemente, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 420 days.

(21) Appl. No.: 11/548,758

(22) Filed: Oct. 12, 2006

(65) Prior Publication Data
US 2007/0185387 A1 Aug. 9, 2007

Related U.S. Application Data

(60) Provisional application No. 60/803,346, filed on May 26, 2006, provisional application No. 60/726,826, filed on Oct. 14, 2005, provisional application No. 60/803,965, filed on Jun. 5, 2006, provisional application No. 60/745,730, filed on Apr. 26, 2006, provisional application No. 60/828,089, filed on Oct. 4, 2006.

(51) Int. Cl.
*A61B 1/32* (2006.01)
(52) U.S. Cl. .......................... 600/208; 600/206; 600/215
(58) Field of Classification Search .................. 600/203, 600/205–208, 21–22, 201, 215, 225, 231, 600/233
See application file for complete search history.

(56) References Cited

U.S. PATENT DOCUMENTS 558,364 A 4/1896 Doolittle
(Continued)

FOREIGN PATENT DOCUMENTS

EP 1 125 552 8/2001
(Continued)

OTHER PUBLICATIONS

Neil Sheehan, Supplemental Expert Report of Neil Sheehan, Re: U.S. Patent No. 5,741,298, United States District Court for the Central District of California, Civil Action No. SACV 03-1322 JVS, Aug. 9, 2005.

(Continued)

*Primary Examiner* — Eduardo C Robert
*Assistant Examiner* — Christina Negrelli
(74) *Attorney, Agent, or Firm* — Pui Tong Ho; David G. Majdali

(57) ABSTRACT

An incrementally adjustable wound retractor, which provides access to a body cavity, includes an inner ring having a diameter greater than the desired diameter of the wound incision, an outer ring having an annular axis and a diameter greater than the desired diameter of the wound incision, and a flexible sleeve disposed in a generally cylindrical form between the inner and outer rings. The outer ring includes first and second circular tubes spaced apart axially with each including a lumen having a rigid, noncompliant split hoop placed therein. The outer ring may be rolled over itself and around the annular axis to retract the sleeve with sufficient force to stretch the incision to the desired diameter. A gel cap seal may be coupled to the outer ring outside of the biological body to seal the opening produced by the wound retractor between the body cavity and outside the body cavity.

26 Claims, 15 Drawing Sheets

U.S. PATENT DOCUMENTS

| | | | |
|---|---|---|---|
| 1,157,202 A | 10/1915 | Bates et al. | |
| 1,810,466 A | 6/1931 | Deutsch | |
| 2,305,289 A | 12/1942 | Coburg | |
| 2,478,586 A | 8/1949 | Krapp | |
| 2,812,758 A | 11/1957 | Blumenschein | |
| 2,835,253 A | 5/1958 | Borgeson | |
| 2,853,075 A | 9/1958 | Hoffman et al. | |
| 3,039,468 A | 6/1962 | Price | |
| 3,111,943 A | 11/1963 | Orndorff | |
| 3,195,934 A | 7/1965 | Parrish | |
| 3,244,169 A | 4/1966 | Baxter | |
| 3,332,417 A | 7/1967 | Blanford, et al. | |
| 3,347,226 A | 10/1967 | Harrower | |
| 3,347,227 A | 10/1967 | Harrower | |
| 3,397,692 A | 8/1968 | Creager, Jr., et al. | |
| 3,402,710 A | 9/1968 | Paleschuck | |
| 3,416,520 A | 12/1968 | Creager, Jr. | |
| 3,447,533 A | 6/1969 | Spicer | |
| 3,523,534 A | 8/1970 | Nolan | |
| 3,717,151 A | 2/1973 | Collett | |
| 3,831,583 A | 8/1974 | Edmunds, Jr. et al. | |
| 3,841,332 A | 10/1974 | Treacle | |
| 3,850,172 A | 11/1974 | Cazalis | |
| 3,856,021 A | 12/1974 | McIntosh | |
| 3,860,274 A * | 1/1975 | Ledstrom et al. | 285/312 |
| 4,024,872 A | 5/1977 | Muldoon | |
| 4,043,328 A | 8/1977 | Cawood, Jr. et al. | |
| 4,069,913 A | 1/1978 | Harrigan | |
| 4,083,370 A | 4/1978 | Taylor | |
| 4,188,945 A | 2/1980 | Wenander | |
| 4,217,664 A | 8/1980 | Faso | |
| 4,222,126 A | 9/1980 | Boretos et al. | |
| 4,254,973 A | 3/1981 | Benjamin | |
| 4,338,937 A | 7/1982 | Lerman | |
| 4,367,728 A | 1/1983 | Mutke | |
| 4,369,284 A | 1/1983 | Chen | |
| 4,454,873 A | 6/1984 | Laufenberg et al. | |
| 4,475,548 A | 10/1984 | Muto | |
| 4,550,713 A | 11/1985 | Hyman | |
| 4,553,537 A | 11/1985 | Rosenberg | |
| 4,691,942 A | 9/1987 | Ford | |
| 4,714,749 A | 12/1987 | Hughes et al. | |
| 4,755,170 A | 7/1988 | Golden | |
| 4,777,943 A | 10/1988 | Chvapil | |
| 4,798,594 A | 1/1989 | Hillstead | |
| 4,802,694 A | 2/1989 | Vargo | |
| 4,842,931 A | 6/1989 | Zook | |
| 4,856,502 A | 8/1989 | Ersfeld et al. | |
| 4,863,438 A | 9/1989 | Gauderer et al. | |
| 4,889,107 A | 12/1989 | Kaufman | |
| 4,895,565 A | 1/1990 | Hillstead | |
| 4,903,710 A | 2/1990 | Jessamine et al. | |
| 4,911,974 A | 3/1990 | Shimizu et al. | |
| 4,926,882 A | 5/1990 | Lawrence | |
| 4,950,223 A | 8/1990 | Silvanov | |
| 4,984,564 A | 1/1991 | Yuen | |
| 4,991,593 A | 2/1991 | LeVahn | |
| 4,998,538 A | 3/1991 | Charowsky et al. | |
| 5,009,224 A | 4/1991 | Cole | |
| 5,015,228 A | 5/1991 | Columbus et al. | |
| 5,037,379 A | 8/1991 | Clayman et al. | |
| 5,082,005 A | 1/1992 | Kaldany | |
| 5,159,921 A | 11/1992 | Hoover | |
| 5,178,162 A | 1/1993 | Bose | |
| 5,192,301 A | 3/1993 | Kamiya et al. | |
| 5,207,656 A | 5/1993 | Kranys | |
| 5,213,114 A | 5/1993 | Bailey, Jr. | |
| 5,259,366 A | 11/1993 | Reydel et al. | |
| 5,262,468 A | 11/1993 | Chen | |
| 5,299,582 A | 4/1994 | Potts | |
| 5,316,541 A | 5/1994 | Fischer | |
| 5,336,708 A | 8/1994 | Chen | |
| 5,350,364 A | 9/1994 | Stephens et al. | |
| 5,353,786 A | 10/1994 | Wilk | |
| 5,366,478 A | 11/1994 | Brinkerhoff et al. | |
| 5,368,545 A | 11/1994 | Schaller et al. | |
| 5,380,288 A | 1/1995 | Hart et al. | |
| 5,389,080 A | 2/1995 | Yoon | |
| 5,389,081 A | 2/1995 | Castro | |
| 5,407,433 A | 4/1995 | Loomas | |
| 5,429,609 A | 7/1995 | Yoon | |
| 5,437,683 A | 8/1995 | Neumann et al. | |
| 5,441,486 A | 8/1995 | Yoon | |
| 5,456,284 A | 10/1995 | Ryan et al. | |
| 5,460,616 A | 10/1995 | Weinstein et al. | |
| 5,476,475 A | 12/1995 | Gadberry | |
| 5,480,410 A | 1/1996 | Cuschieri et al. | |
| 5,486,426 A | 1/1996 | McGee et al. | |
| 5,492,304 A | 2/1996 | Smith et al. | |
| 5,496,280 A | 3/1996 | Vandenbroek et al. | |
| 5,503,112 A | 4/1996 | Luhman et al. | |
| 5,508,334 A | 4/1996 | Chen | |
| 5,514,133 A | 5/1996 | Golub et al. | |
| 5,518,278 A | 5/1996 | Sampson | |
| 5,522,791 A | 6/1996 | Leyva | |
| 5,524,644 A | 6/1996 | Crook | |
| 5,531,758 A | 7/1996 | Uschold et al. | |
| 5,545,179 A | 8/1996 | Williamson, IV | |
| 5,562,677 A | 10/1996 | Hildwein et al. | |
| 5,603,702 A | 2/1997 | Smith et al. | |
| 5,628,732 A | 5/1997 | Antoon, Jr. et al. | |
| 5,632,284 A | 5/1997 | Graether | |
| 5,634,911 A | 6/1997 | Hermann et al. | |
| 5,634,936 A | 6/1997 | Linden et al. | |
| 5,634,937 A | 6/1997 | Mollenauer et al. | |
| 5,636,645 A | 6/1997 | Ou | |
| 5,640,977 A | 6/1997 | Leahy et al. | |
| 5,649,550 A | 7/1997 | Crook | |
| 5,653,705 A | 8/1997 | de la Torre et al. | |
| 5,672,168 A | 9/1997 | de la Torre et al. | |
| 5,681,341 A | 10/1997 | Lunsford et al. | |
| 5,709,664 A | 1/1998 | Vandenbroek et al. | |
| 5,720,730 A | 2/1998 | Blake, III | |
| 5,728,103 A | 3/1998 | Picha et al. | |
| 5,741,298 A | 4/1998 | MacLeod | |
| 5,753,150 A | 5/1998 | Martin et al. | |
| 5,760,117 A | 6/1998 | Chen | |
| 5,782,817 A | 7/1998 | Franzel et al. | |
| 5,788,676 A | 8/1998 | Yoon | |
| 5,792,119 A | 8/1998 | Marx | |
| 5,795,290 A | 8/1998 | Bridges | |
| 5,803,919 A | 9/1998 | Hart et al. | |
| 5,803,921 A | 9/1998 | Bonadio | |
| 5,803,923 A | 9/1998 | Singh-Derewa et al. | |
| 5,810,721 A | 9/1998 | Mueller et al. | |
| 5,813,409 A | 9/1998 | Leahy et al. | |
| 5,814,026 A | 9/1998 | Yoon | |
| 5,819,375 A | 10/1998 | Kastner | |
| 5,832,925 A | 11/1998 | Rothrum | |
| 5,841,298 A | 11/1998 | Huang | |
| 5,853,395 A | 12/1998 | Crook et al. | |
| 5,865,729 A | 2/1999 | Meehan et al. | |
| 5,865,807 A | 2/1999 | Blake, III | |
| 5,871,474 A | 2/1999 | Hermann et al. | |
| 5,895,377 A | 4/1999 | Smith et al. | |
| 5,899,208 A | 5/1999 | Bonadio | |
| 5,904,703 A | 5/1999 | Gilson | |
| 5,906,577 A | 5/1999 | Beane et al. | |
| 5,919,476 A | 7/1999 | Fischer et al. | |
| 5,947,922 A | 9/1999 | MacLeod | |
| 5,951,588 A | 9/1999 | Moenning | |
| 5,957,888 A | 9/1999 | Hinchliffe | |
| 5,957,913 A | 9/1999 | de la Torre | |
| 5,962,572 A | 10/1999 | Chen | |
| 5,964,781 A | 10/1999 | Mollenauer et al. | |
| 5,989,233 A | 11/1999 | Yoon | |
| 5,989,266 A | 11/1999 | Foster | |
| 5,993,471 A | 11/1999 | Riza et al. | |
| 5,993,485 A | 11/1999 | Beckers | |
| 5,997,515 A | 12/1999 | de la Torre et al. | |
| 6,010,494 A | 1/2000 | Schafer et al. | |
| 6,024,736 A | 2/2000 | de la Torre et al. | |
| 6,025,067 A | 2/2000 | Fay | |
| 6,033,426 A | 3/2000 | Kaji | |
| 6,033,428 A | 3/2000 | Sardella | |
| 6,035,559 A | 3/2000 | Freed et al. | |
| 6,045,535 A | 4/2000 | Ben Nun | |

| | | |
|---|---|---|
| 6,053,934 A | 4/2000 | Andrews |
| 6,077,288 A | 6/2000 | Shimomura |
| 6,090,043 A | 7/2000 | Austin et al. |
| 6,110,154 A | 8/2000 | Shimomura et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,162,172 A | 12/2000 | Cosgrove et al. |
| 6,224,612 B1 | 5/2001 | Bates |
| 6,238,373 B1 | 5/2001 | de la Torre |
| 6,254,533 B1 | 7/2001 | Fadem et al. |
| 6,254,534 B1 | 7/2001 | Butler et al. |
| 6,276,661 B1 | 8/2001 | Laird |
| 6,287,280 B1 | 9/2001 | Lampropoulos |
| 6,319,246 B1 | 11/2001 | de la Torre |
| 6,325,384 B1 | 12/2001 | Berry, Sr. et al. |
| 6,382,211 B1 | 5/2002 | Crook |
| 6,383,162 B1 | 5/2002 | Sugarbaker |
| 6,413,244 B1 | 7/2002 | Bestetti et al. |
| 6,440,063 B1 | 8/2002 | Beane et al. |
| 6,450,983 B1 | 9/2002 | Rambo |
| 6,482,181 B1 | 11/2002 | Racenet et al. |
| 6,485,435 B1 | 11/2002 | Bakal |
| 6,533,734 B1 | 3/2003 | Corley, III et al. |
| 6,551,344 B2 | 4/2003 | Thill |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,613,952 B2 | 9/2003 | Rambo |
| 6,623,426 B2 | 9/2003 | Bonadio et al. |
| 6,702,787 B2 | 3/2004 | Racenet et al. |
| 6,723,044 B2 | 4/2004 | Pulford et al. |
| 6,814,078 B2 | 11/2004 | Crook |
| 6,846,287 B2 | 1/2005 | Bonadio et al. |
| 6,866,861 B1 | 3/2005 | Luhman |
| 6,895,965 B2 | 5/2005 | Scarberry et al. |
| 6,902,541 B2 | 6/2005 | McNally et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,997,909 B2 | 2/2006 | Goldberg |
| 7,033,319 B2 | 4/2006 | Pulford et al. |
| 7,052,454 B2 | 5/2006 | Taylor |
| 7,081,089 B2 | 7/2006 | Bonadio et al. |
| 7,163,510 B2 * | 1/2007 | Kahle et al. ............... 600/208 |
| 7,214,185 B1 | 5/2007 | Rosney |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0038077 A1 | 3/2002 | de la Torre et al. |
| 2002/0072762 A1 | 6/2002 | Bonadio et al. |
| 2003/0040711 A1 | 2/2003 | Racenet et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael et al. |
| 2004/0015185 A1 | 1/2004 | Ewers et al. |
| 2004/0049100 A1 | 3/2004 | Butler et al. |
| 2004/0073090 A1 | 4/2004 | Butler et al. |
| 2004/0092796 A1 | 5/2004 | Butler et al. |
| 2004/0106942 A1 | 6/2004 | Taylor et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0254426 A1 | 12/2004 | Wenchell |
| 2004/0267096 A1 | 12/2004 | Caldwell et al. |
| 2005/0020884 A1 | 1/2005 | Hart et al. |
| 2005/0033246 A1 | 2/2005 | Ahlberg et al. |
| 2005/0059865 A1 * | 3/2005 | Kahle et al. ............... 600/206 |
| 2005/0090717 A1 | 4/2005 | Bonadio et al. |
| 2005/0148823 A1 | 7/2005 | Vaugh et al. |
| 2005/0155611 A1 | 7/2005 | Vaugh et al. |
| 2005/0197537 A1 | 9/2005 | Bonadio et al. |
| 2005/0222582 A1 | 10/2005 | Wenchell |
| 2005/0241647 A1 | 11/2005 | Nguyen et al. |
| 2005/0261720 A1 | 11/2005 | Caldwell |
| 2005/0267419 A1 | 12/2005 | Smith |
| 2005/0283050 A1 | 12/2005 | Gundlapalli et al. |
| 2005/0288558 A1 | 12/2005 | Ewers et al. |
| 2006/0030755 A1 | 2/2006 | Ewers et al. |
| 2006/0047284 A1 | 3/2006 | Gresham |
| 2006/0052669 A1 | 3/2006 | Hart |
| 2006/0084842 A1 | 4/2006 | Hart et al. |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161050 A1 | 7/2006 | Butler et al. |
| 2007/0149859 A1 * | 6/2007 | Albrecht et al. ............... 600/208 |

FOREIGN PATENT DOCUMENTS

| | | |
|---|---|---|
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | 950266 | 4/1995 |
| IE | S950266 | 4/1995 |
| IE | S75368 | 8/1997 |
| IE | S960196 | 8/1997 |
| IE | S970810 | 11/1997 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 11-290327 | 10/1999 |
| JP | 2002-28163 | 1/2002 |
| JP | 02003 235879 A | 8/2003 |
| WO | WO95/07056 | 3/1995 |
| WO | WO95/22289 | 8/1995 |
| WO | WO 95/24864 | 9/1995 |
| WO | WO 95/27468 | 10/1995 |
| WO | WO 97/11642 | 4/1997 |
| WO | WO 98/19853 | 5/1998 |
| WO | WO 98/35614 | 8/1998 |
| WO | WO 98/48724 | 11/1998 |
| WO | WO 99/15068 | 4/1999 |
| WO | WO 99/25268 | 5/1999 |
| WO | WO00/32116 | 6/2000 |
| WO | WO 00/35356 | 6/2000 |
| WO | WO 00/32120 | 8/2000 |
| WO | WO00/54675 | 9/2000 |
| WO | WO00/54676 | 9/2000 |
| WO | WO00/54677 | 9/2000 |
| WO | WO01/08581 | 2/2001 |
| WO | WO 01/26559 | 4/2001 |
| WO | WO02/34108 | 5/2002 |
| WO | WO03/032819 | 4/2003 |
| WO | WO03/034908 | 5/2003 |
| WO | WO03/061480 | 7/2003 |
| WO | WO 03/077726 | 9/2003 |
| WO | WO 2004/075730 | 9/2004 |
| WO | WO 2004/075741 | 9/2004 |
| WO | WO 2004/075930 | 9/2004 |
| WO | WO 2005/034766 | 4/2005 |

OTHER PUBLICATIONS

Dexterity Protractor Instruction Manual by Dexterity Surgical, Inc.
Horigane, et al., Technical Note: Development of a Duodoenal Cannula for Sheep, Journal of Animal Science, Apr. 1992, vol. 70, Issue 4, pp. 1216-1219.
Horigane, et al., Silicone Rumen Cannula with a Soft Cylindrical Part and a Hard Flange, Journal of Dairy Science, Nov. 1989, vol. 72, No. 11, pp. 3230-3232.
McSweeney, Cannullation of the Rumen in Cattle and Buffaloes Australian Veterinary Journal, Aug. 1989, vol. 66, No. 8, pp. 266-268.
Yamazaki et al., Diurnal Changes in the Composition of Abomasal Digesta in Fasted and Fed Sheep, The Tohoku Journal of Argircultural Research, Mar. 1987, vol. 37, No. 3-4, pp. 49-58.
The International Bureau of WIPO International Preliminary Report on Patentability dated Apr. 16, 2008 for PCT Application No. PCT/US2006/039799.
European Patent Office, International Search Report and The Written Opinion of the International Searching Authority for PCT Application No. PCT/US2006/039799 mailed Mar. 27, 2007.
Co-Pending U.S. Appl. No. 10/381,220, filed Mar. 20, 2003, Title: Surgical Access Apparatus and Method.
Co-Pending U.S. Appl. No. 10/516,198, filed Nov. 30, 2004, Title: Wound Retractor.
Co-Pending U.S. Appl. No. 10/927,551, filed Aug. 25, 2004, Title: Surgical Access System.
Co-Pending U.S. Appl. No. 11/244,647, filed Oct. 5, 2005, Title: Surgical Access Apparatus and Method.
Co-Pending U.S. Appl. No. 11/245,709, filed Oct. 7, 2005, Title: Surgical Access System.
Co-Pending U.S. Appl. No. 11/330,661, filed Jan. 12, 2006, Title: Sealed Surgical Access Device.
Co-Pending U.S. Appl. No. 11/548,746, filed Oct. 12, 2006, Title: Method of Making a Hand Access Laparoscopic Device.
Co-Pending U.S. Appl. No. 11/755,305, filed May 30, 2007, Title: Wound Retraction Apparatus and Method.
Co-Pending U.S. Appl. No. 11/548,765, filed Oct. 12, 2006, Title: Split Hoop Wound Retractor.
Co-Pending U.S. Appl. No. 11/548,767, filed Oct. 12, 2006, Title: Circular Surgical Retractor.
Co-Pending U.S. Appl. No. 11/548,781, filed Oct. 12, 2006, Title: Wound Retractor With Gel Cap.
Co-Pending U.S. Appl. No. 11/548,955, filed Oct. 12, 2006, Title: Hand Access Laparoscopic Device.
Co-Pending U.S. Appl. No. 11/564,409, filed Nov. 29, 2006, Title: Surgical Instrument Access Device.
US 5,344,646, Chen (withdrawn).
Co-Pending U.S. Appl. No. 12/108,400, filed Apr. 23, 2008, Title: Wound Retraction Apparatus and Method.
European Patent Office, International Search Report and The Written Opinion of the International Searching Authority for International Application No. PCT/2006/039883, mailed Jan. 31, 2007.
European Patent Office, International Search Report and The Written Opinion of the International Searching Authority for International Application No. PCT/2006/039905 mailed Jan. 17, 2007.
European Patent Office, International Search Report and The Written Opinion of the International Searching Authority for International Application No. PCT/2006/040073 mailed Jan. 26, 2007.
International Searching Authority/US, International Search Report and The Written Opinion of the International Searching Authority for International Application No. PCT/US04/05484.
International Searching Authority/US, International Search Report and The Written Opinion of the International Searching Authority for International Application No. PCT/US01/29682.
The International Bureau of WIPO, International Preliminary Report on Patentability dated Apr. 16, 2008 for PCT Application No. PCT/US2006/039799.
The International Bureau of WIPO, International Preliminary Report on Patentability, dated Aug. 29, 2006, for International Application No. PCT/US2004/028250.
The International Bureau of WIPO, International Preliminary Report on Patentability for International Application No. PCT/US2006/039800 dated Apr. 16, 2008.
European Patent Office, International Search Report and The Written Opinion of the International Searching Authority for International Application No. PCT/US2006/040154, dated Jan. 23, 2007.
Declaration of John R. Brustad Under 37 C.F. R. 1.132, dated Dec. 10, 2009.
"Applied GelPort™ Advanced Access Device" product sales brochure dated 2001.
"Cap Ring" production drawing dated Jan. 19, 2001.
"Gelport® Laparoscopic Hand Access System" product sales brochure dated 2005.
"Cap Ring Medium" production drawing dated Aug. 16, 2005.

* cited by examiner

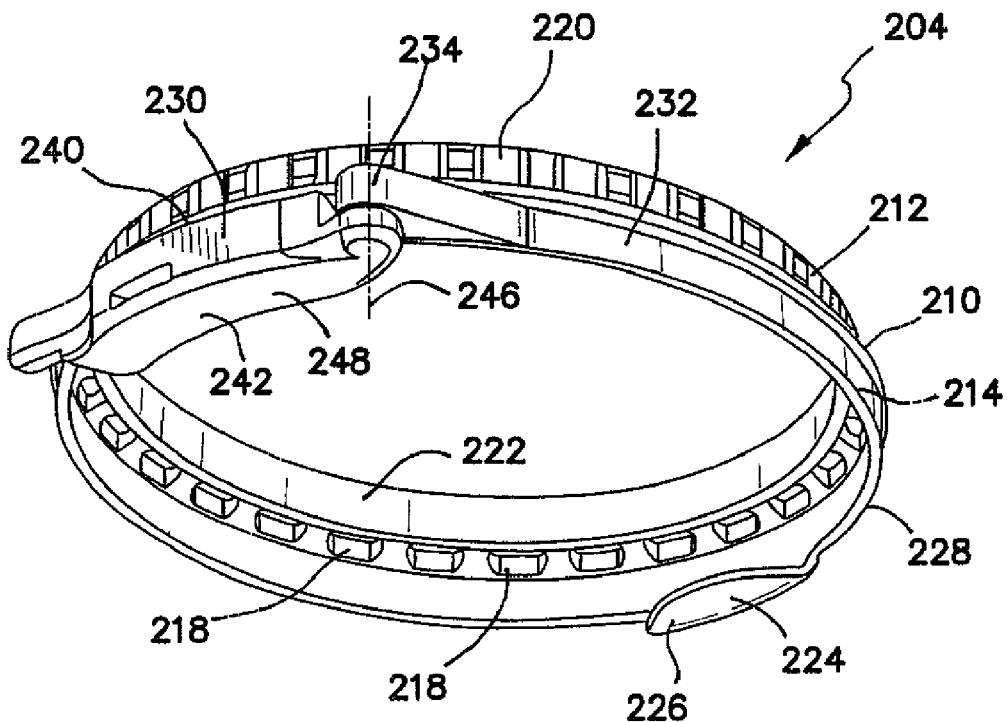
FIG. 17
FIG. 18
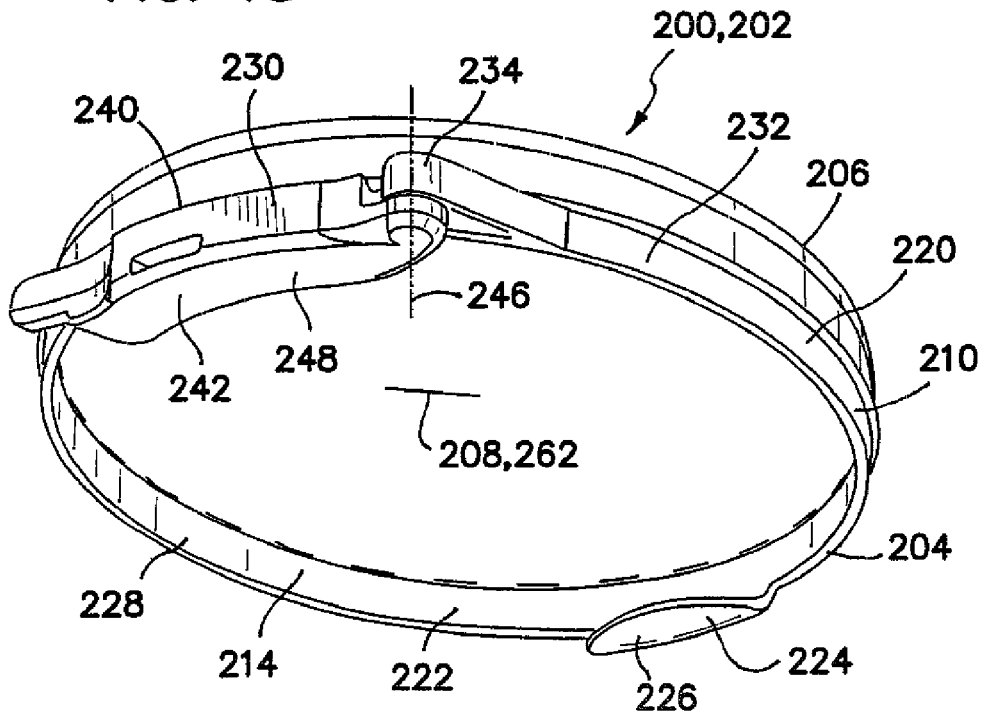

SPLIT HOOP WOUND RETRACTOR WITH GEL PAD

BACKGROUND

This invention relates substantially to devices and other apparatuses facilitating sealed access with surgical instruments, such as a surgeon's hand, across a body wall and into a body cavity.

In several areas of surgery there exists a need to have mechanisms or devices that can seal a body cavity or space, and yet permit the introduction of surgical instruments such as guidewires, endoscopes, and even the hand of a surgeon. Typical of these areas of surgery is laparoscopic surgery that relies on surgical instruments inserted through the abdominal wall to reach an operative site within the abdominal cavity. In order to increase space around the operative site within the cavity, insufflation gases are typically introduced to inflate the cavity and elevate the abdominal wall. The pressurizing of the abdominal cavity is referred to as pneumoperitoneum in this context, the need to seal the body cavity or space arises from the need to maintain the pneumoperitoneum even when instruments are present.

Trocars have been commonly used to provide instrument access in laparoscopic surgeries. These trocars have included elaborate seal structures having zero seals that prevent the escape of the gases in the absence of instruments, and instrument seals that prevent the escape of the gases in the presence of instruments. Unfortunately, the instrument seals have been able to accommodate only a narrow range of instrument diameters. Multiple seal pairs had to be provided where wider ranges were desired.

Some instruments, such as the hand of the surgeon, have been too large for trocar access. Under these circumstances, hand-assisted laparoscopic seals have been provided. Such devices have been large, cumbersome, and largely ineffective in providing the required sealing mechanism. Other access devices, such as Touhy-Borst seals, have been used, but only for very small diameter access such as that required by a guidewire.

Each of the prior devices suffers from drawbacks that make the device difficult or cumbersome to use. For example, a Touhy-Borst seal requires two hands to use and does not form a seal when a guidewire or other device is about to be introduced. Present trocar seals and hand-assisted seals require two valves, one forming an instrument seal in the presence of the instrument, and the other forming a zero seal in the absence of the instrument. For example, in hand-assisted devices, elaborate mechanisms have been required to seal around the surgeons arm. When the arm is removed, a separate zero seal has been required to prevent the escape of blood or insufflation gases.

SUMMARY

The invention is directed to a gel cap that is adapted for being coupled to a wound retractor. The wound retractor has a substantially noncompliant outer ring that is adapted for juxtaposition with an outer surface of a biological body wall and for disposition relative to an incision in the body wall. The wound retractor also includes an inner ring that is adapted for juxtaposition with an inner surface of the biological body wall and for disposition relative to the incision in the body wall. The wound retractor further includes a sleeve that is adapted to traverse the incision in the body wall. The sleeve of the wound retractor couples the outer ring to the inner ring. The wound retractor is adapted to retract and seal the incision. The gel cap includes a cap ring, a lever, means for hinging the lever to the cap ring, and a gel pad. The cap ring includes a substantially cylindrical ring having a first, proximal portion, a second, distal portion, and a longitudinal axis extending through the proximal and distal portions. The cap ring also includes a lip at a distal end of the distal portion of the cap ring. The lip curves radially inward from the wall of the distal portion of the cap ring and extends around a portion of the circumference of the cap ring. The gel cap also includes a lever that is positioned at the distal portion of the cap ring and substantially opposite the lip at the distal portion of the cap ring. The lever swings on a plane that is substantially perpendicular to the axis of the cap ring. The lever includes a proximal end, a distal end, and a first, distal substantially flat lip positioned at the distal end of the lever. The distal lip of the lever lies in a plane that is positioned substantially perpendicular to the axis of the cap ring. The gel pad is made of a gel material. The gel pad is coupled to the cap ring and is positioned at the proximal portion of the cap ring. The gel pad includes an access portion for providing a passage from external the body to a body cavity. The passage of the gel pad forms an instrument seal in the presence of an instrument inserted therethrough and a zero seal in the absence of an instrument inserted therethrough. In a first, open state the lever is swung outwardly, away from the body of the cap ring to provide clearance for inserting the outer ring of the wound retractor into the gel cap. In a second, closed state the lever is swung toward the cap ring such that the distal lip of the lever protrudes radially inwardly from the body of the lever and radially inwardly through the wall of the cap ring. In the second state, with the outer ring of the wound retractor positioned in the distal portion of the cap ring, the distal lip of the lever is configured to abut the distal surface of the outer ring of the wound retractor and secure the gel cap to the wound retractor. The lip of the cap ring and the distal lip of the lever are configured to receive the outer ring of the wound retractor such that the outer ring of the wound retractor is positioned between the lip of the cap ring and the distal lip of the lever at the distal end of the outer ring of the wound retractor and the gel pad at the proximal end of the outer ring of the wound retractor. The gel pad is adapted to be placed in juxtaposition with the incision.

In one aspect of the invention, the proximal portion of the cap ring includes a plurality of apertures that are distributed about the circumference of the cap ring. The apertures extend through the wall of the proximal potion of the cap ring. In one aspect, the gel of the gel pad covers and fills the apertures. In another aspect, the gel in the apertures connects the gel at an outer portion of the cap ring to the gel at an inner portion of the cap ring. In another aspect, the gel of the gel cap extends into the distal portion of the cap ring. In one aspect, the distal portion of the cap ring is adapted to receive the outer ring of the wound retractor such that the outer ring of the wound retractor embeds into the gel pad at the distal portion of the cap ring and displaces the gel, thereby forming a seal between the gel pad and the outer ring and sleeve of the wound retractor. In another aspect, the access portion of the gel pad includes a plurality of intersecting dead-end slits. In another aspect, the lip at the distal end of the distal portion of the cap ring extends about 30° around the circumference of the cap ring. In another aspect, the cap ring is made of a polymer. In one aspect, the cap ring is made of polyethylene, while in another aspect the cap ring is made of polycarbonate. In another aspect, the gel pad covers and seals the entire opening in the cap ring. In another aspect, the gel pad is adapted to cover substantially the entire wound opening. In another aspect, the outer surface of the cap ring includes a lug, and the lever is coupled to the lug. In one aspect, the lug includes an aperture that extends substantially parallel to the longitudinal axis of the cap ring. The lever includes a hinge pin that extends substantially perpendicular to the distal lip of the lever. The aperture of the lug is adapted to receive the hinge pin of the lever. In a similar aspect, the lug includes the hinge pin and the lever includes the aperture. In another aspect, the lever includes locking means for facilitating prevention of unintended opening of the lever from the second state to the first state. In one aspect, the locking means includes a first aperture or groove in the wall of the distal portion of the cap ring. The aperture or groove receives and supports the distal lip of the lever. The distal lip of the lever includes a latch that is adapted for engaging the first aperture or groove in the distal portion of the cap ring through which the distal lip of the lever protrudes when the lever is in the second state. In one aspect, the distal lip of the lever includes a catch that protrudes proximally therefrom. The catch is adapted to engage the outer ring of the wound retractor at a position on the inner circumference of the outer ring In another aspect, the distal lip on the lever extends around about 60° of the circumference of the cap ring when the lever is in the second state. In another aspect, the lever includes a second, proximal substantially flat lip that is positioned at the proximal end of the lever and lies in a plane that is substantially parallel to the distal lip of the lever, and the wall of the distal portion of the cap ring includes a second aperture for receiving the proximal lip of the lever. In one aspect, the distal and proximal lips of the lever extend from the same side of the lever. In one aspect, the lever includes locking means for facilitating the prevention of unintended opening of the lever from the second state to the first state. In one aspect, the proximal lip of the lever includes a latch that is adapted for engaging the second aperture in the distal portion of the cap ring through which the proximal lip of the lever protrudes when the lever is in the second state. In one aspect, the proximal lip on the lever extends around about 45° of the circumference of the cap ring when the lever is in the second state. In another aspect, the gel cap includes more than one lever with the levers being substantially equally spaced between each other and the lip on the cap ring.

These and other features and advantages of the invention will become more apparent with a discussion of embodiments in reference to the associated drawings

BRIEF DESCRIPTION OF THE DRAWINGS

FIG. 2b illustrates a perspective view of the wound retractor of FIG. 2a;

FIG. 17 is a bottom perspective view of a cap ring of the gel cap of FIG. 16;

FIG. 18 is a bottom perspective view of the gel cap of FIG. 16;

DETAILED DESCRIPTION

Figure 1:
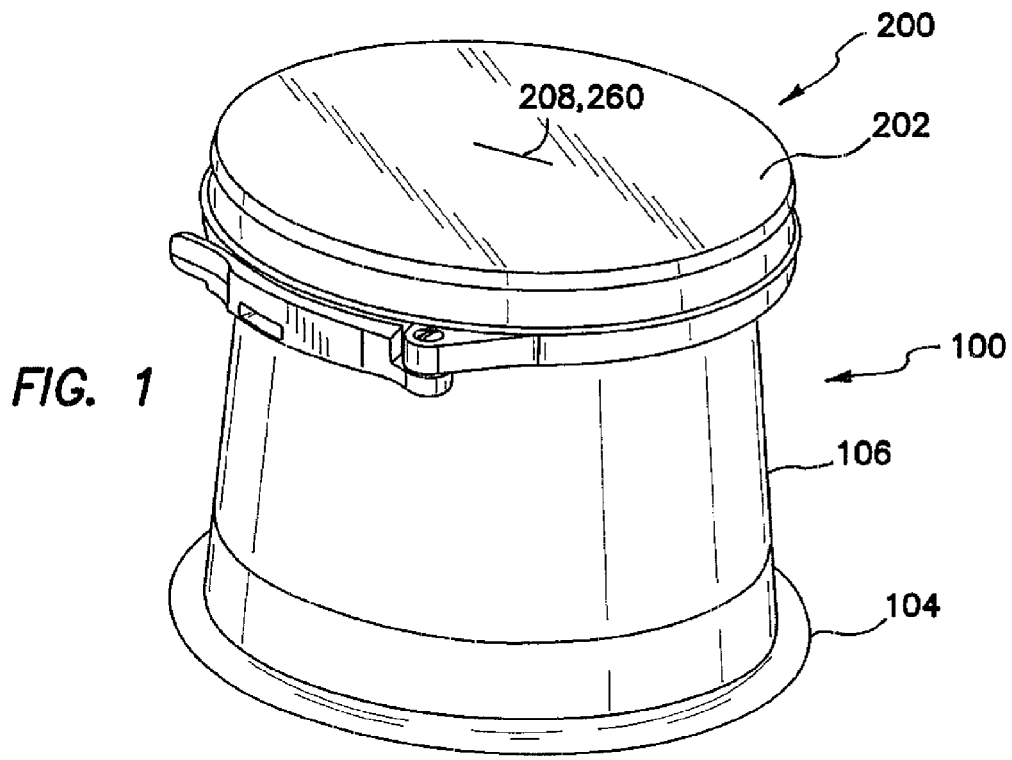
FIG. 1 is a top perspective view of a gel cap of the invention placed onto a wound retractor of the invention.
Figure 2A:
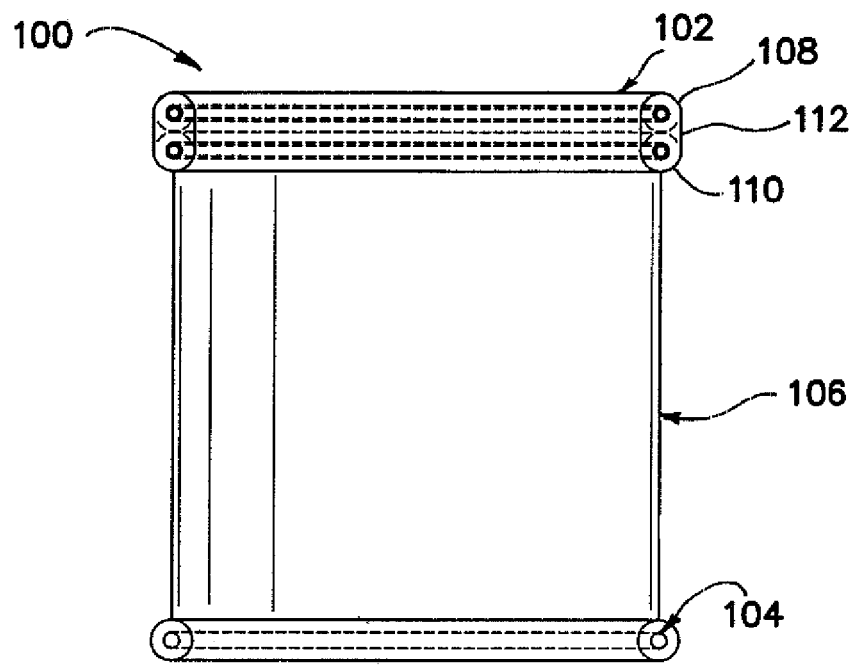
FIG. 2a illustrates an elevation view of an incrementally adjustable wound retractor in accordance with an embodiment of the invention.
Figure 2B:
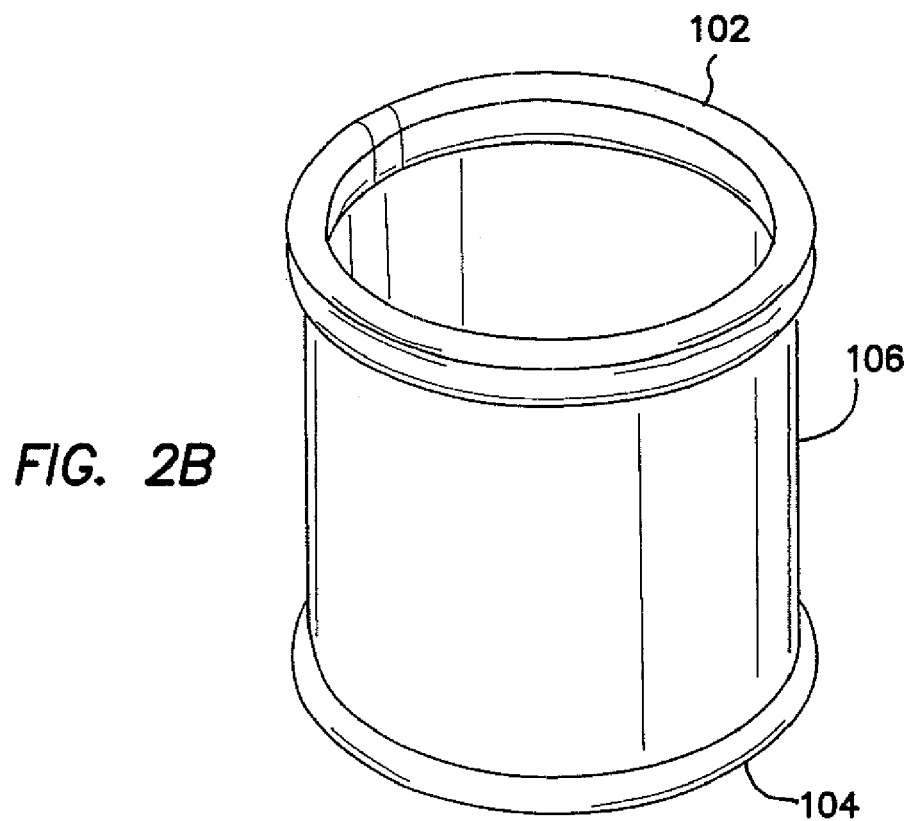
Figure 8:
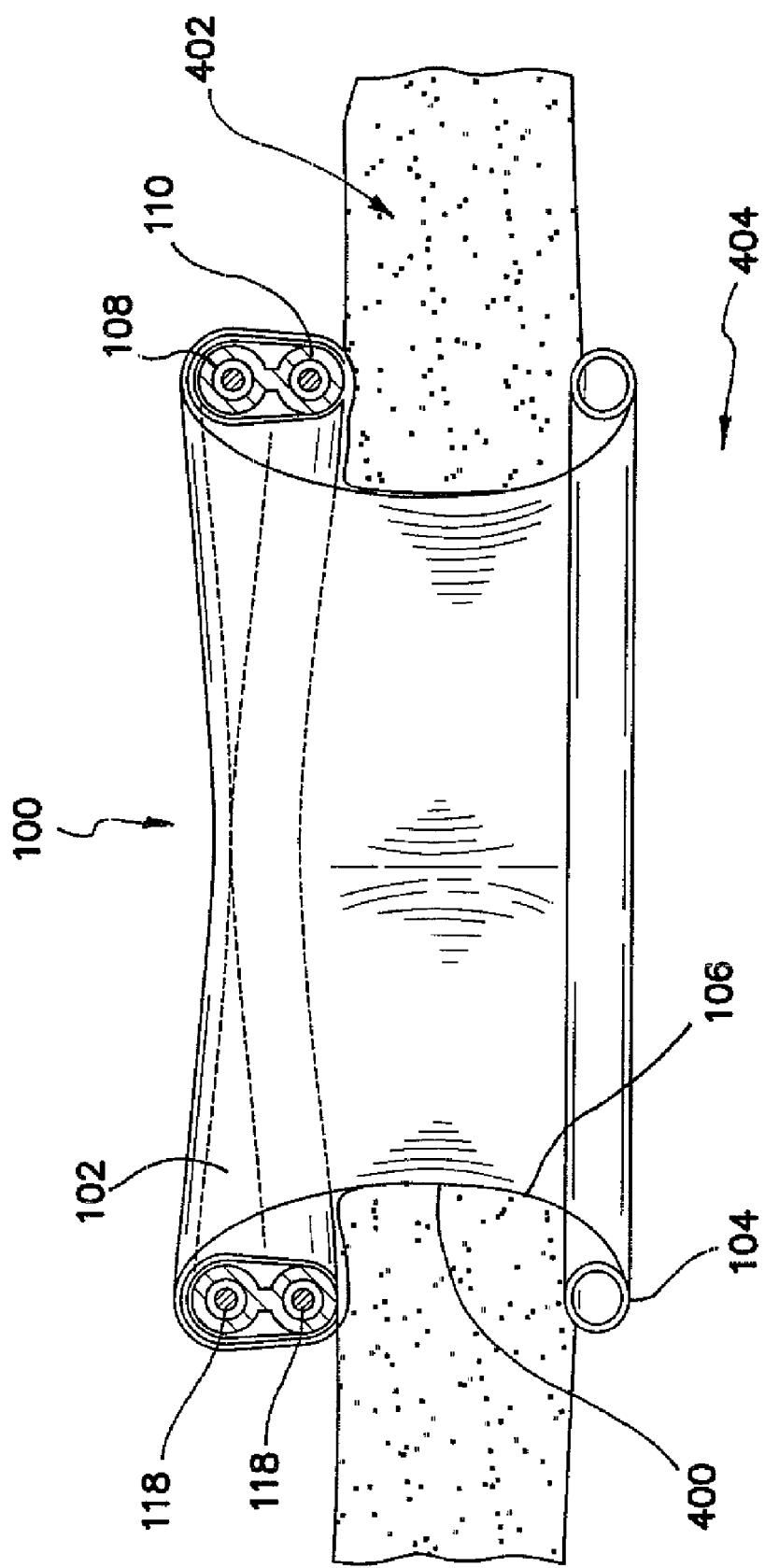
FIG. 8 illustrates the wound retractor of FIG. 1 deployed in an incision.
Figure 10:
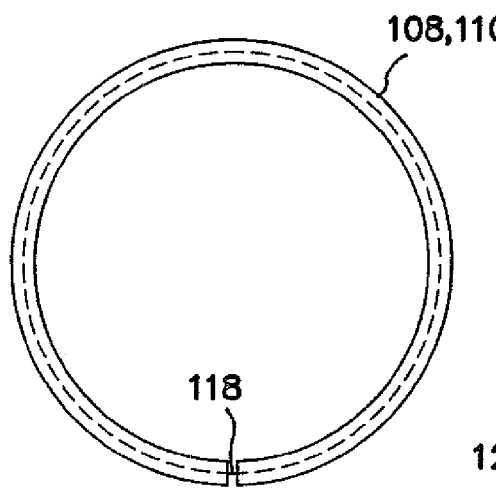
FIG. 10 depicts a plan view of one of the first and second circular tubes of the outer ring with a split hoop placed therein with the split hoop and circular tube in their neutral state.
Figure 11:
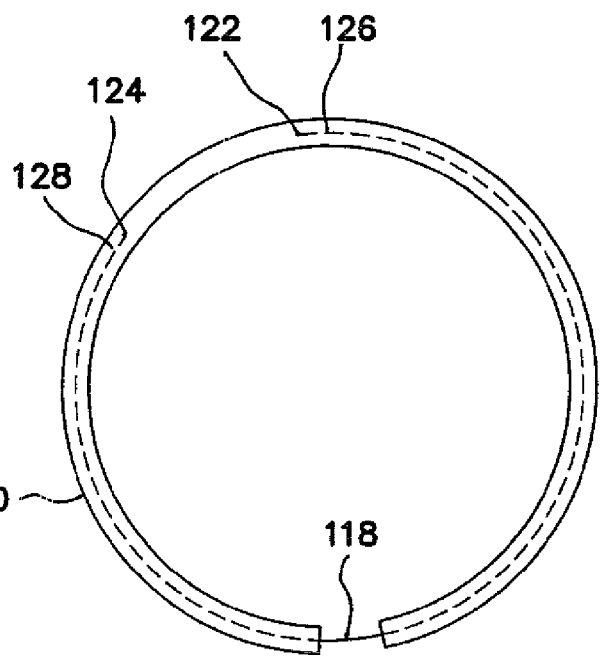
FIG. 11 depicts a plan view of one of the first and second circular tubes of the outer ring with a split hoop placed therein with the split hoop and circular tube in their expanded state.
Figure 12:
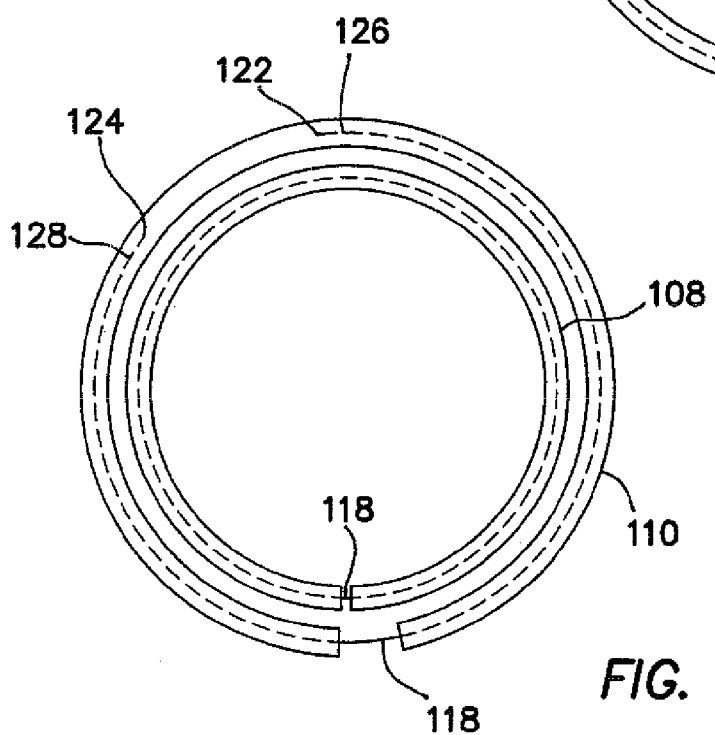
FIG. 12 depicts a plan view of the first circular tube and split hoop and the second circular tube and split hoop with the first circular tube and split hoop in their neutral state and the second circular tube and split hoop in their expanded state being rolled around the first circular tube and split hoop
Figure 13:
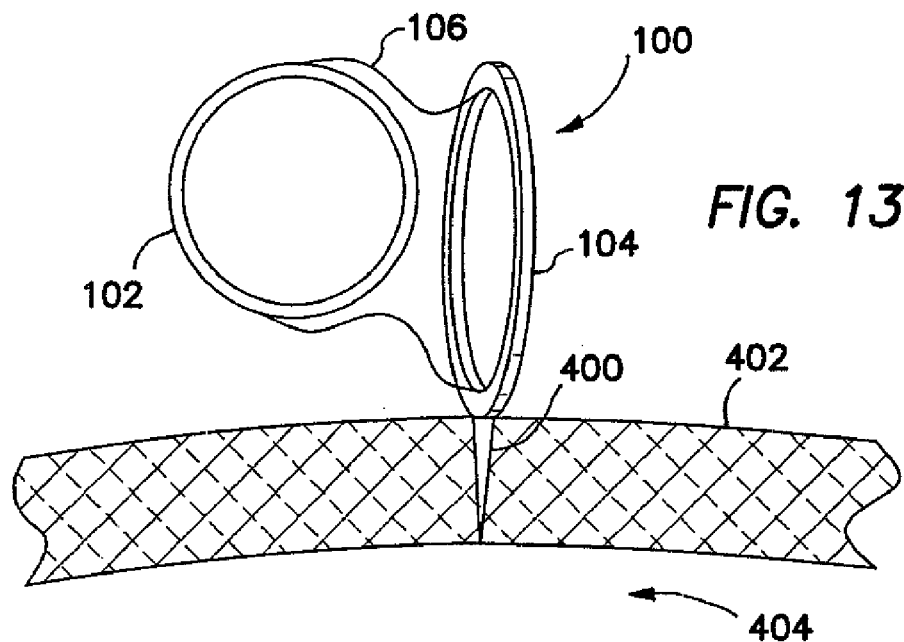
FIG. 13 is a side view of a wound retractor of the invention being inserted into a wound in a body wall with the inner ring being inserted into the wound.
Figure 14:
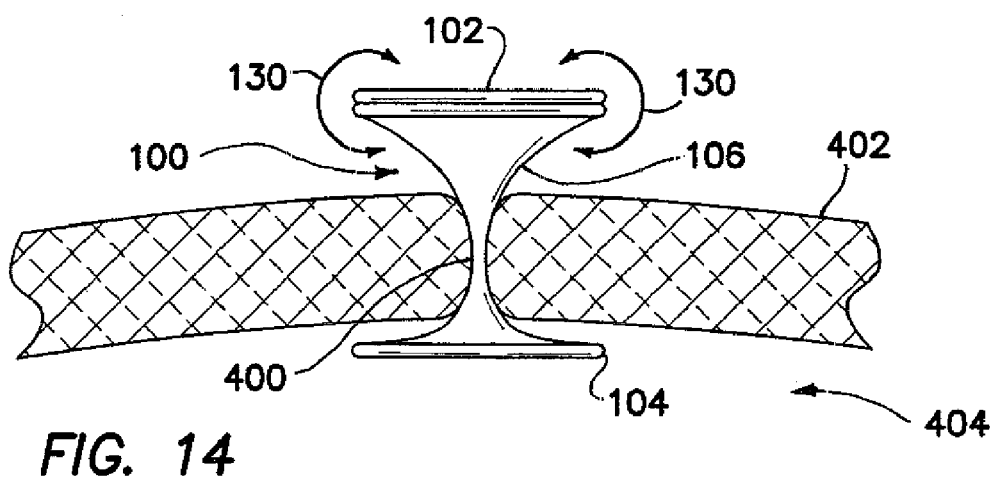
FIG. 14 is a side view of the wound retractor of the invention placed in the wound in the body wall and depicting a direction for rolling the outer ring to retract the wound.
Figure 15:
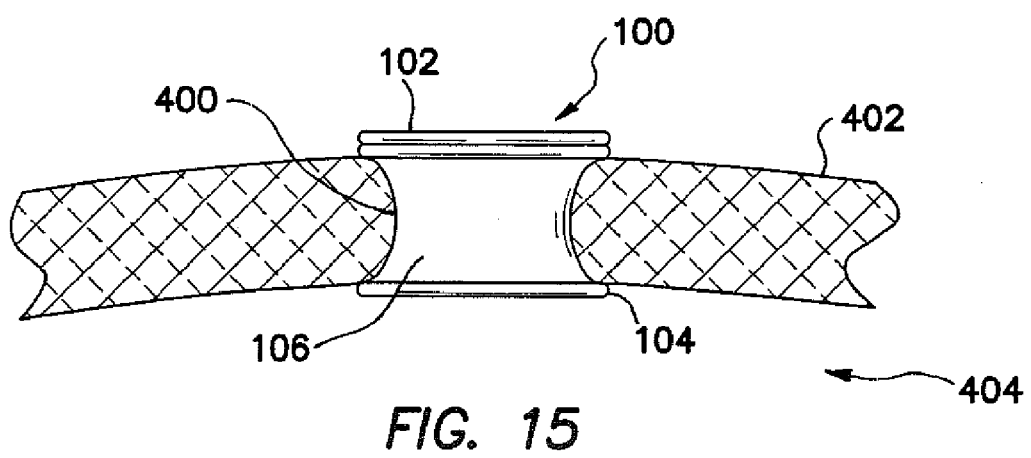
FIG. 15 is a side view of the wound retractor invention placed in the wound in the body wall with the wound retracted.
Figure 16:
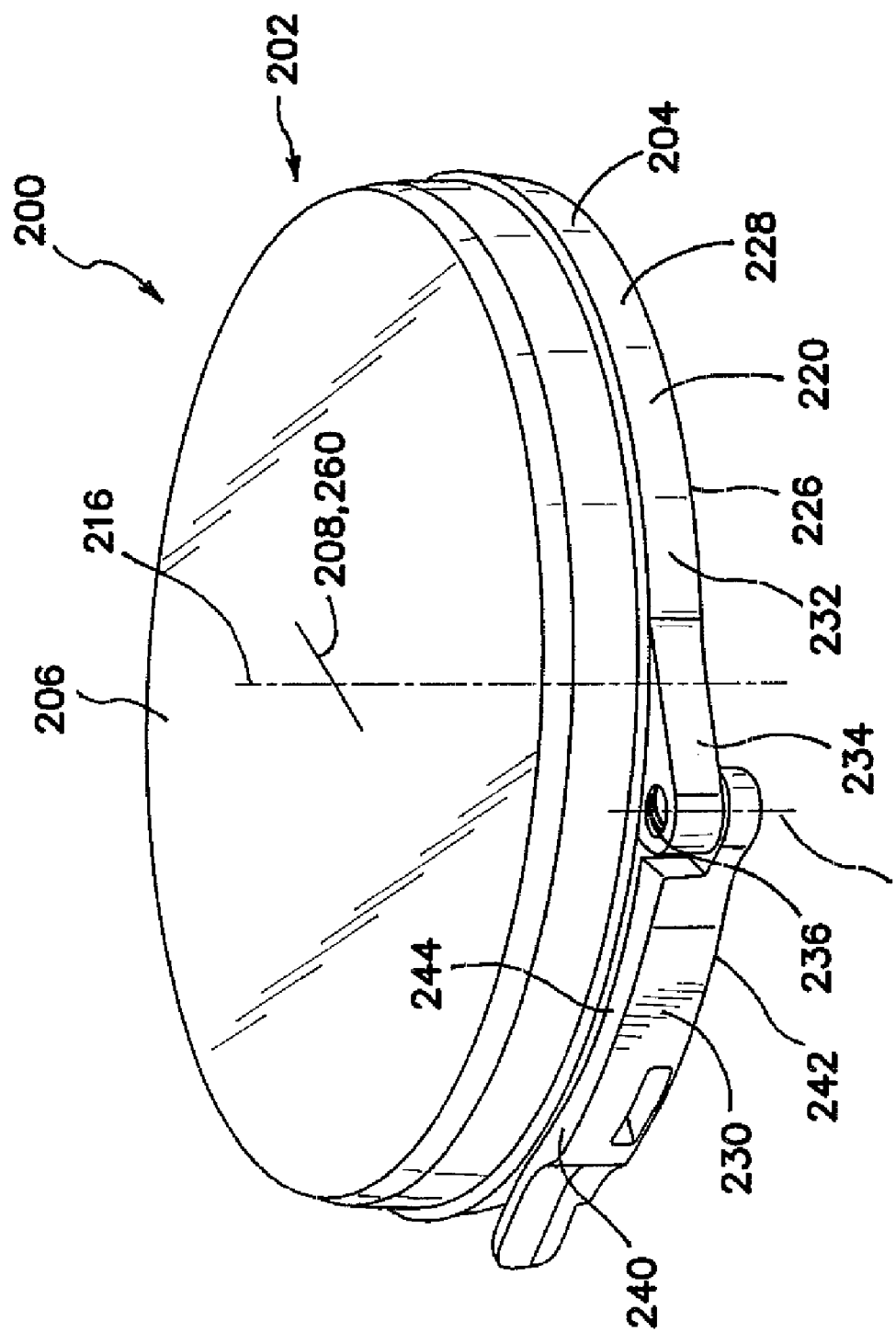
FIG. 16 is a top perspective view of a gel cap having a lever for coupling the gel cap to the outer ring of a wound retractor.
Figure 19:
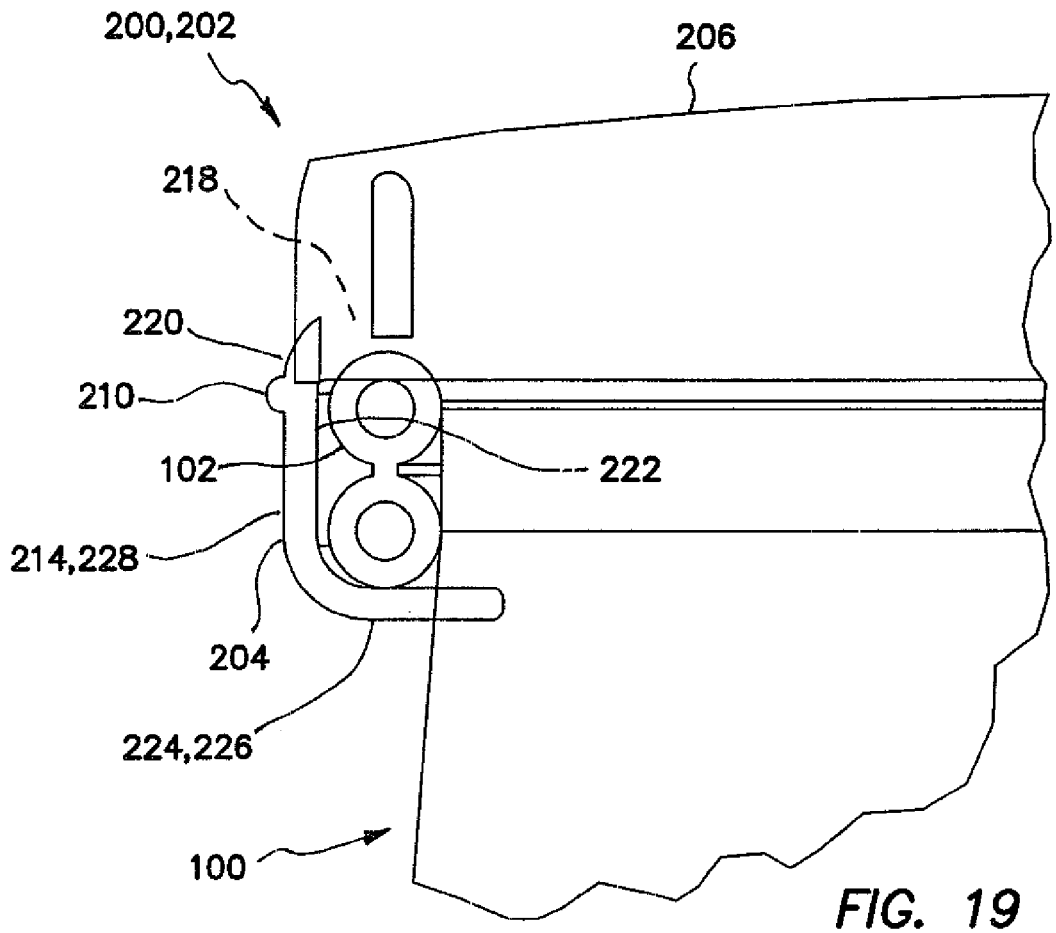
FIG. 19 is a partial section view of the gel cap of FIG. 16 coupled to the outer ring of the wound retractor.
Figure 20:
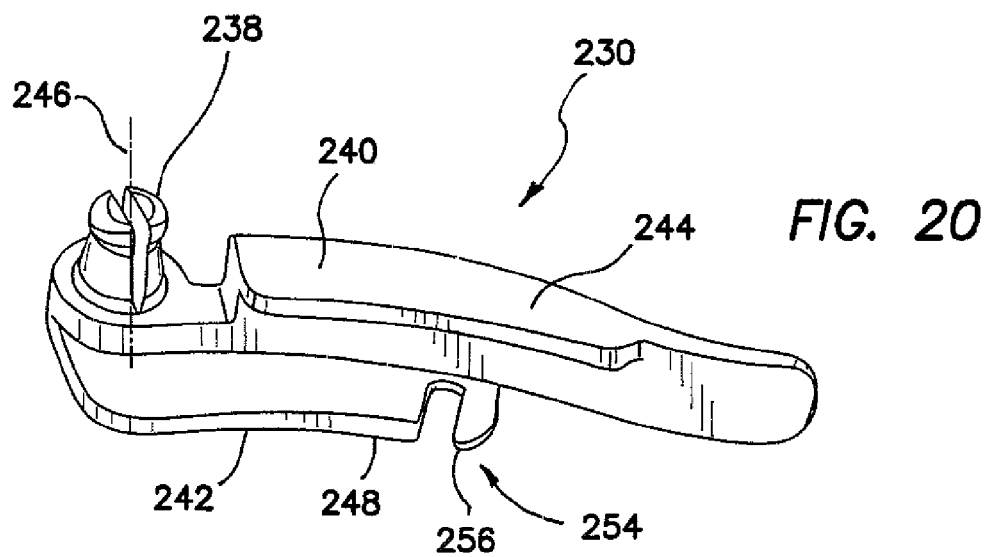
FIG. 20 is a top perspective view of the lever portion of the gel cap of FIG. 16.
Figure 21:
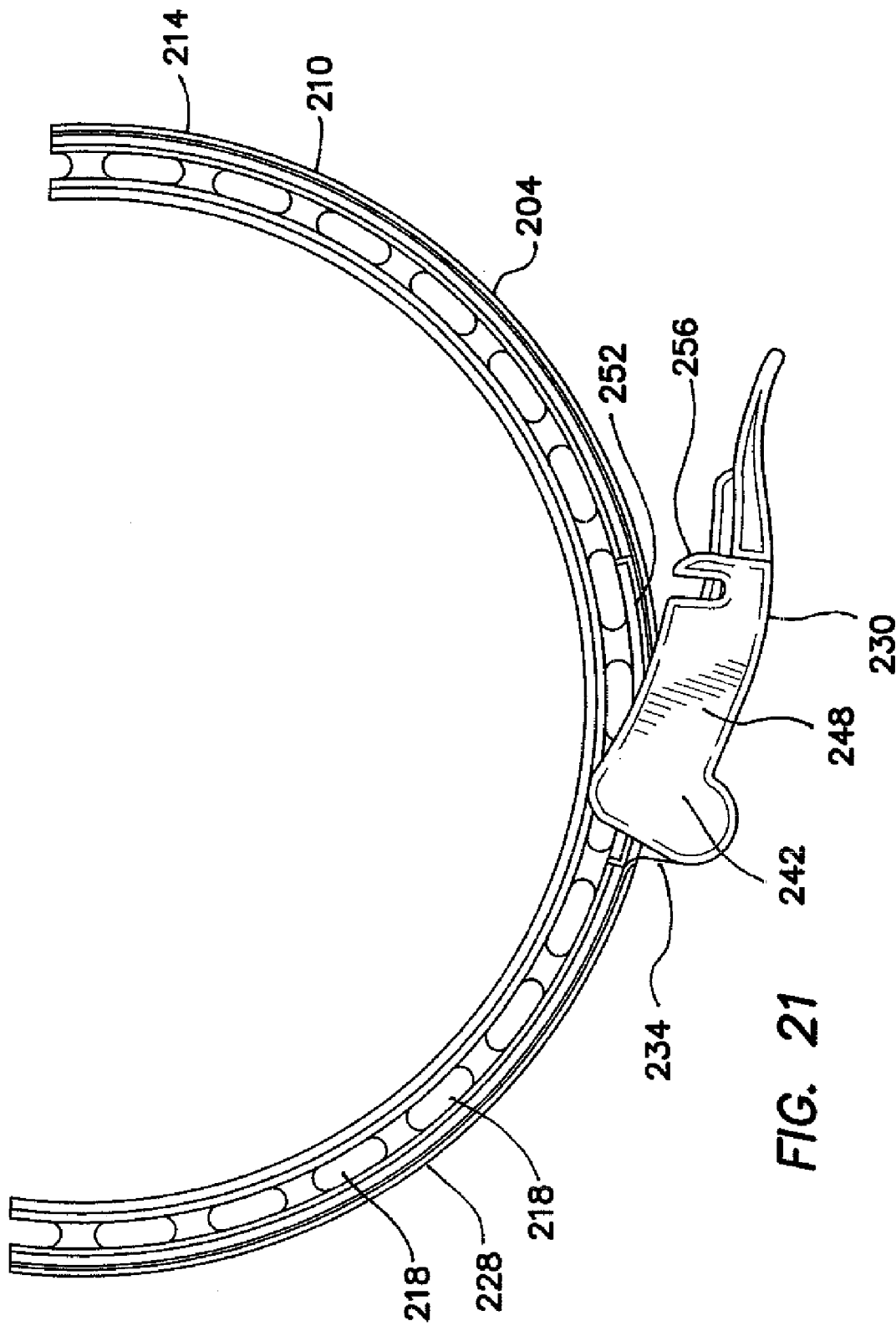
FIG. 21 is a partial bottom view of the cap ring of FIG. 16 with the lever in a first, open state.
Figure 22:
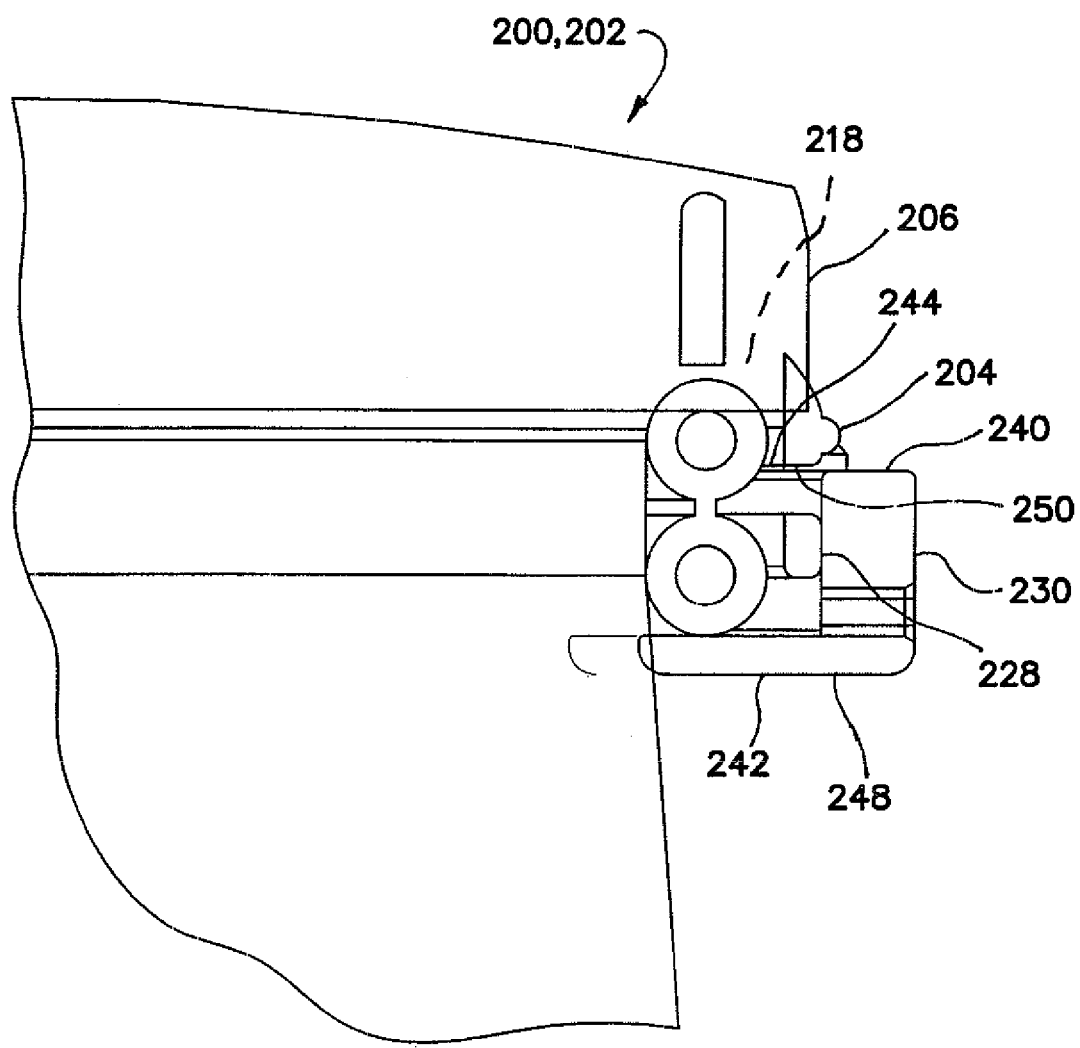
FIG. 22 is a partial section view of the gel cap of FIG. 16 coupled to the outer ring of the wound retractor with the lever in a second, closed state.

FIGS. 1, 2a and 2b illustrate a wound retractor 100 and gel cap 202 in accordance with an embodiment of the invention. The wound retractor 100 includes a double-tube outer ring 102, an inner ring 104, and a distensible sleeve 106 coupling the outer ring 102 to the inner ring 104. The sleeve 106 may be coupled to the outer ring 102 and the inner ring 104 by heat seal, adhesive, or other means that are well known in the art. The sleeve 106 may be made of a material that is flexible and impermeable to fluids and bacteria. The inner ring 104 may be made of materials having sufficient hardness to retain its shape after insertion of the inner ring into a body cavity 404 (FIG. 8). The materials of which the outer ring 102 is made must allow the outer ring 102 to be turned around its annular axis as further described below and illustrated in FIGS. 3a-3c. The shape of the outer ring 102 affects both its ability to grip and to provide stability during and after adjustment. The double-tube outer ring 102 includes a first circular tube 108 and a second circular tube 110 that are separated axially and may be coupled together by a small web 112. Each of the circular tubes 108 and 110 includes a lumen.

Figure 4:
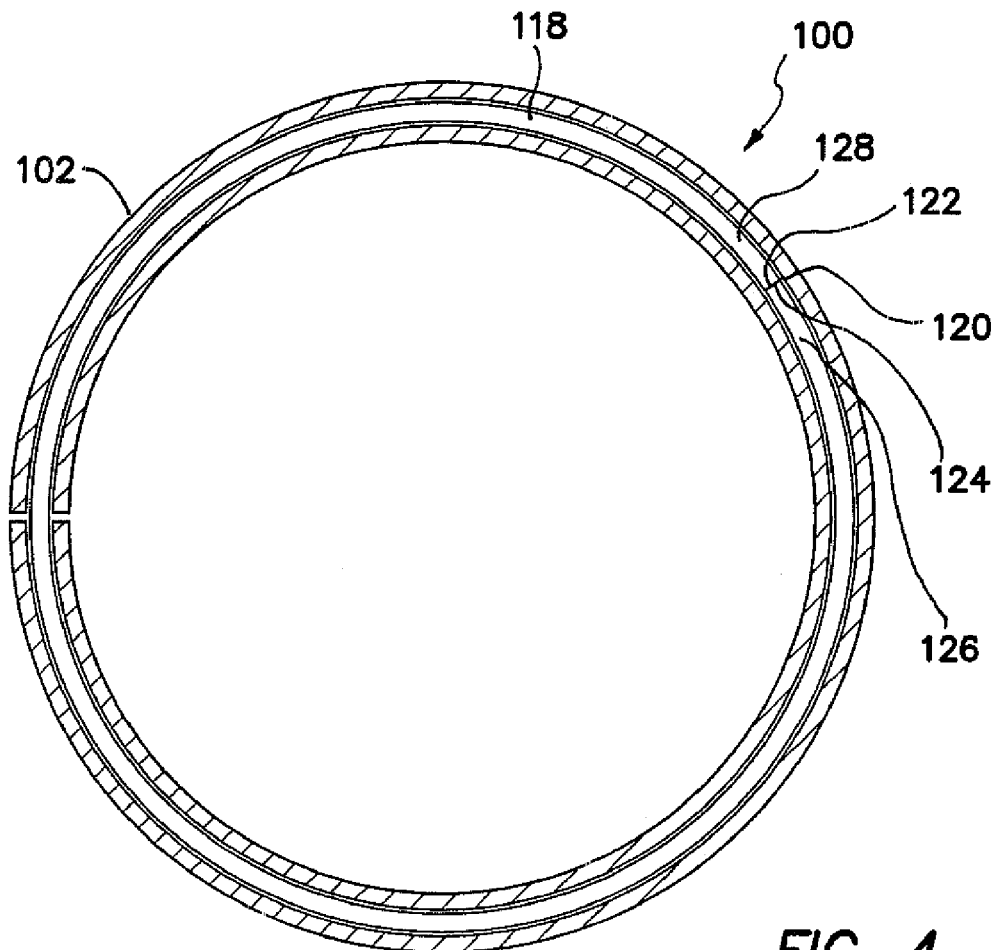
FIG. 4 depicts a plan view, in cross section, of the outer ring of the wound retractor having a split hoop in a lumen thereof.
Figure 5:
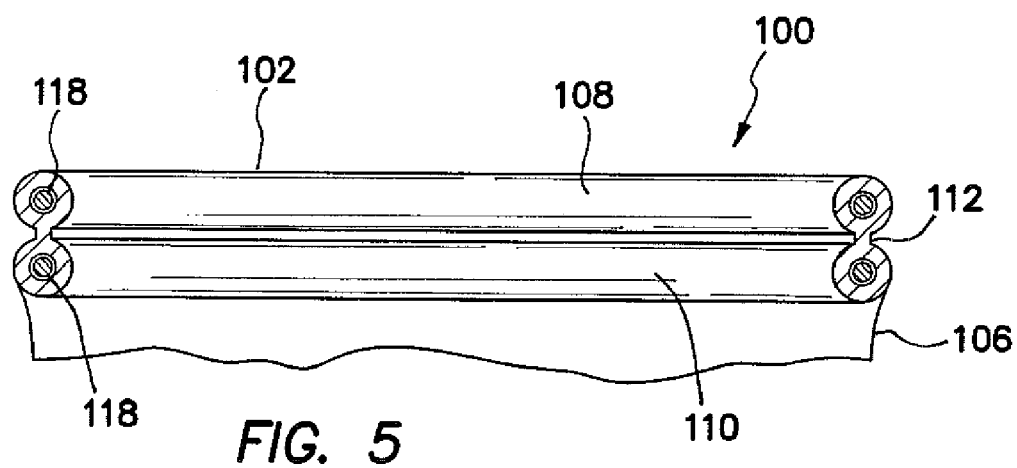
FIG. 5 depicts an elevation view of the outer ring of the wound retractor having a split hoop in the lumen of each of the first and second circular tubes of the outer ring.
Figure 6:
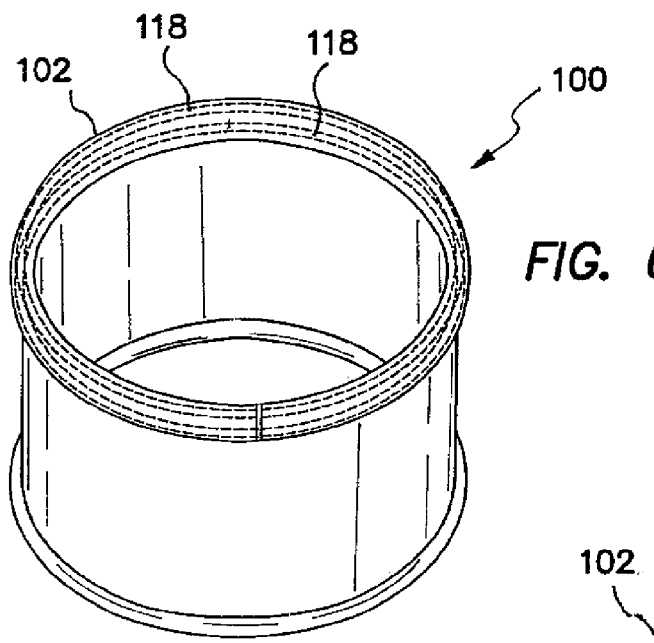
FIG. 6 depicts a perspective view of the wound retractor.

Referring to FIGS. 4-6, a wound retractor 100 may include the double-tube outer ring 102 having a substantially noncompliant, split hoop 118 positioned in the lumen of the first circular tube 108 and a substantially noncompliant, split hoop 118 positioned in the lumen of the second circular tube 110. Each of the split hoops 118 includes a hoop having a single split 120 about its circumference with the split creating a first end 122 of the split hoop and a second end 124 of the split hoop. In its neutral position, the first and second ends 122, 124 of the respective split hoops 118 substantially abut each other.

The substantially noncompliant hoops 118 may be made of metals, such as stainless steel, piano wire heat treated to a spring temper, or other metals that produce a substantially noncompliant hoop. The substantially noncompliant hoops 118 may also be formed of rigid polymeric materials through molding, machining, and other processes that are well known in the art. The substantially noncompliant hoops 118 may also be formed of other suitable rigid materials that are well known in the art.

Figure 7A:
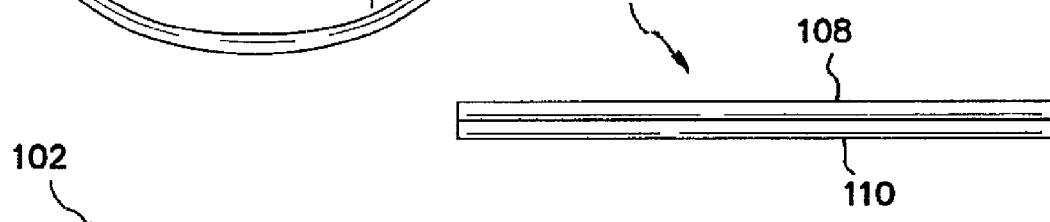
FIGS. 7a-7b illustrate different processes of forming the outer ring of the invention.
Figure 7B:
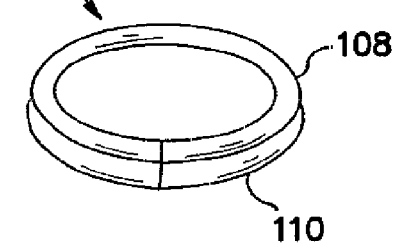
Figure 9:
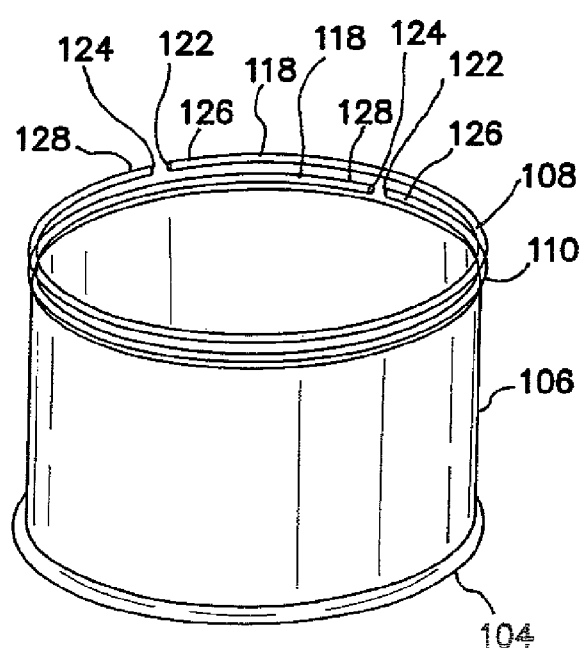
FIG. 9 depicts a perspective view of the wound retractor having the split hoops in the lumen of each of the first and second circular tubes of the outer ring.

As shown in FIGS. 7a-7b, the outer ring 102 may be formed by transforming an extruded elastomeric double-tube into a circular ring by placing the split hoops 118 (FIGS. 4-6) into the first and second circular tubes 108, 110. This is accomplished by inserting one of the first and second ends 122, 124 of one of the hoops 118 into the lumen of the first circular tube 108 and one of the first and second ends of the other hoop 118 into the lumen of the second circular tube 110. The split hoops 118 are continually fed into the lumens until substantially each of the entire hoops 118 is within the respective circular tubes 108, 110. The extruded elastomeric tube 102 takes on the circular shape of the split hoops 118 placed in the lumens of the first and second circular tubes 108, 110.

It is appreciated that the outer ring 102 can be designed in various configurations and sizes to achieve various retraction rates and/or to conform to different body surfaces. The lumens of the first and second circular tubes 108, 110 may have cross-sections of different geometries, such as circular, oval, triangular, rectangular, any geometric shape with multiple sides, etc. The split hoops 118 may also have cross-sections of different geometries, such as circular, rectangular, oval, triangular, any geometric shape with multiple sides, etc. Advantages of the above embodiments of the invention include improved retraction adjustability and stability.

With continued reference to FIGS. 4-6 and with reference to FIGS. 7a, 7b and 8-12, with each of the first and second circular tubes 108, 110 including a split hoop 118, it is not necessary to provide means for a first end portion 126 and a second end portion 128 of the split hoop to overlap each other when rolling the sleeve 106 around the outer ring 102. Since the split hoop 118 in the each of the first and second circular tubes 108, 110 has substantially abutting first and second ends 122, 124 and no means are provided for the first and second end portions 126, 128 of the split hoops to overlap each other, each of the split hoops 118 functions as an axle about which the outer ring 102 may turn for half a rotation, or 180°. More particularly, the first circular tube 108 may be rolled outside the second circular tube 110 with the circumference of the split hoop 118 in the first circular tube expanding to clear the split hoop 118 in the second circular tube. Then the second circular tube 110 may be rolled outside the first circular tube 108 with the circumference of the split hoop 118 in the second circular tube expanding to clear the split hoop 118 in the first circular tube (see FIG. 12). These steps may be repeated until the wound 400 is retracted to the desired degree.

FIGS. 3a-3c and FIG. 8 illustrate the retraction and adjustment of the outer ring 102 to fit an incision. In accordance with the invention, the wound retractor 100 is axially adjustable in increments. In particular, the upper end of the sleeve 106 can be wrapped around the outer ring 102 so as to tightly seal the sides or edges of the incision 400. The unique shape of the outer ring 102 provides for an easy snap action when rolled about itself. The outer ring 102 also provides for incremental shortening of the sleeve 106 and for stability after installation.

FIGS. 8 and 13-15 illustrate a process of installing the wound retractor 100 in a wound opening 400. An incision 400 in the shape of a slit is first made in a body wall of a patient, such as the abdominal wall 402. The inner ring 104 is compressed and the inner ring and sleeve 106 are then manually inserted into the body cavity 404 through the incision 400 with the outer ring 102 remaining external the body cavity 404. Once the inner ring 104 is within the body cavity 404, it expands around the inner surface of the incision 400 so as to be generally parallel to the outer surface of the abdominal wall 402. The sleeve 106 provides a working channel from outside the body cavity 404 to inside the body cavity.

Figure 3A:
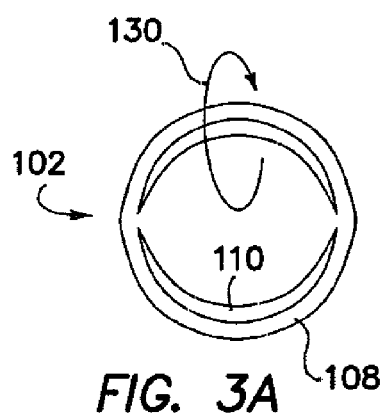
FIGS. 3a-3c illustrate the retraction of the outer ring of the wound retractor of FIG. 1 to retract an incision.
Figure 3B:
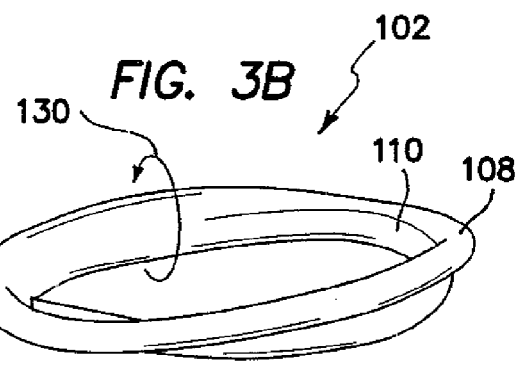
Figure 3C:
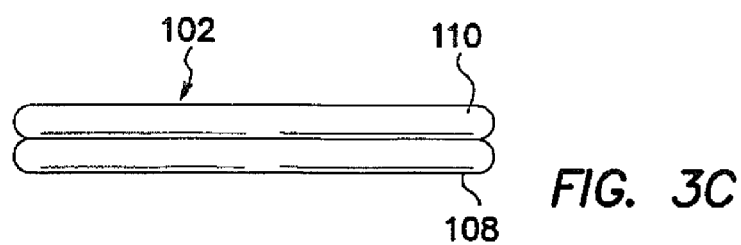

The outer ring 102 initially rests above the abdominal wall 402 around the wound opening 400. Since the upper end of the sleeve 106 is coupled to the outer ring 102, the sleeve 106 can be drawn upwards and radially outward or inward, thereby drawing the inner ring 104 tightly against the inner surface of the abdominal wall 402. Moreover, the intermediate portion of the sleeve 106 is drawn tightly against the sides and edges of the wound opening 400, thereby retracting the adjacent tissue and producing a tightly sealed opening to the body cavity 404. The sleeve 106 contacts the entire surface of the wound 400 and protectively covers and seals it from contamination and infection. Depending on the size and depth of the incision 400, the user can roll up the sleeve 106 by gripping the double-tube outer ring 102 and turning it in a direction 130, as also illustrated in FIGS. 3a-3c, until the sleeve 106 abuts the outer edge of the wound opening 400. The inner ring 104 is adapted for juxtaposition with the inner surface of the abdominal wall 402 and the outer ring 102 is adapted for juxtaposition with the outer surface of the abdominal wall. Both the inner ring 104 and the outer ring 102 are adapted for disposition relative to the incision 400 in the abdominal wall 402. The sleeve 106 is adapted to traverse the incision 400 in the abdominal wall 402.

An advantage of the wound retractor 100 of the present invention is it provides for an easier, faster and higher retraction rate than that known in the prior art, thereby resulting in less traumatic effects to the patient. Another advantage of the wound retractor 100 of the present invention is it provides tactile gripping and incremental rolling of the sleeve 106 about the outer ring 102. In comparison to retractors of the prior art, the substantially noncompliant hoops 118 in the lumens of the outer ring 102 provide greater strength, which in turn provides better retraction. The substantially noncompliant hoops 118 control the shape of the wound opening 400, rather than the wound opening controlling the shape of the wound retractor 100. In this manner, the wound retractor 100 of the present invention provides better isolation, protection, and sealing of the wound 400.

After surgery, the wound retractor 100 may be retrieved by grabbing the inner ring 104 and the sleeve 106 and pulling them through the wound opening 400. The use of the sleeve 106 and the ease of retracting the outer ring 102 provide higher compression between the inner and outer rings. As a result, the wound retractor 100 of the invention provides incremental adjustability to fit a wide range of incision sizes and isolates and protects the wound from bacterial infection as diseased body parts and contaminated instruments are passed through the wound.

Referring to FIGS. 16-25, the surgical access device 200, such as a gel cap 202, is used to seal the opening between the body cavity 404 (see FIG. 8) and the area outside the body cavity while providing access into the body cavity from outside the body cavity. The gel cap 202 includes a cap ring 204 that couples to the outer ring 102 of the wound retractor 100 and a gel pad 206 coupled to the cap ring. The gel pad 206 is made of a gel material and includes an access portion 208 or passage through the gel for providing a passage from external the body to the body cavity 404. In one aspect, the access portion 208 may include a plurality of intersecting dead-end slits 260, 262. The access portion 208 forms an instrument seal in the presence of an instrument, such as the arm of a surgeon, inserted therethrough and a zero seal in the absence of an instrument inserted therethrough. Unlike foam rubber or other similar types of elastic materials, the gel provides a gas tight seal around a variety of shapes and sizes of hands or instruments inserted therethrough.

To combine the gel pad 206 with the cap ring 204, the cap ring may be placed into a mold that includes the shape of the desired gel pad and the uncured gel is added to the mold. Referring to FIG. 17, in one aspect, the cap ring 204 includes a substantially cylindrical ring 210 having a first, proximal portion 212, a second, distal portion 214 and a longitudinal axis 216 extending through the proximal and distal portions. The gel pad 206 is positioned at the proximal portion 212 of the cap ring 204. The proximal portion 212 of the cap ring 204 may include a plurality of apertures 218 distributed about the circumference of the cap ring. The apertures 218 may extend through the wall of the proximal portion 212 of the cap ring 204. Sufficient gel may be added to the mold to cover and fill the apertures 218 (see FIG. 18). When adding uncured gel into the mold, the gel flows through the apertures 218 and remains in the apertures. Also, for reasons that will be described below, sufficient gel may be added to the mold to extend into the distal portion 214 of the cap ring 204. When the gel pad 206 is cured, the gel in the apertures 218 connects the gel at the outer portion 220 of the cap ring 204 to the gel at the inner portion 222 of the cap ring, thus forming a mechanical lock between the gel and the cap ring. Alternatively, as will be described in more detail below, other means may be used to couple the gel pad 206 to the cap ring 204, such as separately forming a gel slug 206 and coupling the gel slug to the inner surface of the proximal portion 212 of the cap ring 204.

The distal portion 214 of the cap ring 204 is substantially cylindrical and is configured to receive the outer ring 102 of the wound retractor 100. In one aspect, the distal portion 214 of the cap ring 204 includes a lip 224 at the distal end 226 thereof (see FIG. 17). The lip 224 curves radially inwardly from the wall 228 of the distal portion 214 of the cap ring 204 and extends around a portion of the circumference of the cap ring. In one aspect, the lip 224 extends around about 30° of the circumference of the cap ring 204; however, the lip may extend longer or shorter distances around the circumference of the cap ring. The lip 224 is configured to receive the distal-most circular tube 108, 110 of the outer ring 102 such that the outer ring is positioned between the lip 224 and the gel pad 206 (see FIG. 19). More particularly, when the outer ring 102 of the wound retractor 100 is received by the distal portion 214 of the cap ring 204, the outer ring of the wound retractor embeds into the gel pad 206 at the distal portion of the cap ring and displaces the gel, thereby forming a seal between the gel pad and the outer ring and sleeve 106 of the wound retractor. This places the gel pad 206 in juxtaposition with the incision 400.

In one aspect, the distal portion 214 of the cap ring 204 also includes a swinging lever 230 (FIG. 16) that swings on a plane that is substantially perpendicular to the axis 216 of the cap ring. In one aspect, the lever 230 is positioned substantially opposite the lip 224 on the distal portion 214 of the cap ring 204. The outer surface 232 of the cap ring 204 may include a lug 234 to which the lever 230 is coupled. In one aspect, the lug 234 includes an aperture 236 extending substantially parallel to the longitudinal axis 216 of the cap ring 204 and is adapted to receive a hinge pin 238 portion of the lever 230. However, those familiar with the art will recognize that the hinge pin may be positioned on the lug and the aperture may be positioned in the lever. Also, other means that are well known in the art may be used to hinge the lever to the cap ring. When coupled to the cap ring 204, the lever 230 includes a proximal end 240 and a distal end 242. The lever 230 includes a first, distal substantially flat lip 244 positioned at the distal end 242 of the lever and lying in a plane that is positioned substantially perpendicular to the axis 246 of the pin 238 on the lever. It should be noted that the axis 246 of the pin 238 on the lever 230 is substantially parallel to the longitudinal axis 216 of the cap ring 204. The lever 230 may also include a second, proximal substantially flat lip 248 positioned at the proximal end 240 of the lever and also lying in a plane that is substantially perpendicular to an axis 246 of the pin 238 on the lever such that the proximal lip of the lever is substantially parallel to the distal lip 244 of the lever. Both of the distal and proximal lips 244, 248 of the lever 230 extend from the same side of the lever.

In a first, open state (FIG. 21), the lever 230 is swung outwardly, away from the body of the cap ring 204 to provide clearance for inserting the outer ring 102 of the wound retractor 100 into the gel cap. In a second, closed state (FIG. 22), the lever 230 is swung toward the cap ring 204 such that the distal and proximal lips 244, 248 of the lever protrude radially inwardly from the body of the lever and radially inwardly through the wall 228 of the cap ring. In one aspect, the wall 228 of the distal portion 214 of the cap ring 204 includes a first aperture 250 or groove for receiving the distal lip 244 of the lever 230. Similarly, the wall 228 of the distal portion 214 of the cap ring 204 also includes a second aperture 252, such as a slot, for receiving and supporting the proximal lip 248 of the lever 230. In one aspect, the distal lip 244 on the lever 230 extends around about 60° of the circumference of the cap ring and the proximal lip 248 on the lever extends around about 45° of the circumference of the cap ring; however, the distal and proximal lips may extend longer or shorter distances around the circumference of the cap ring.

Figure 23:
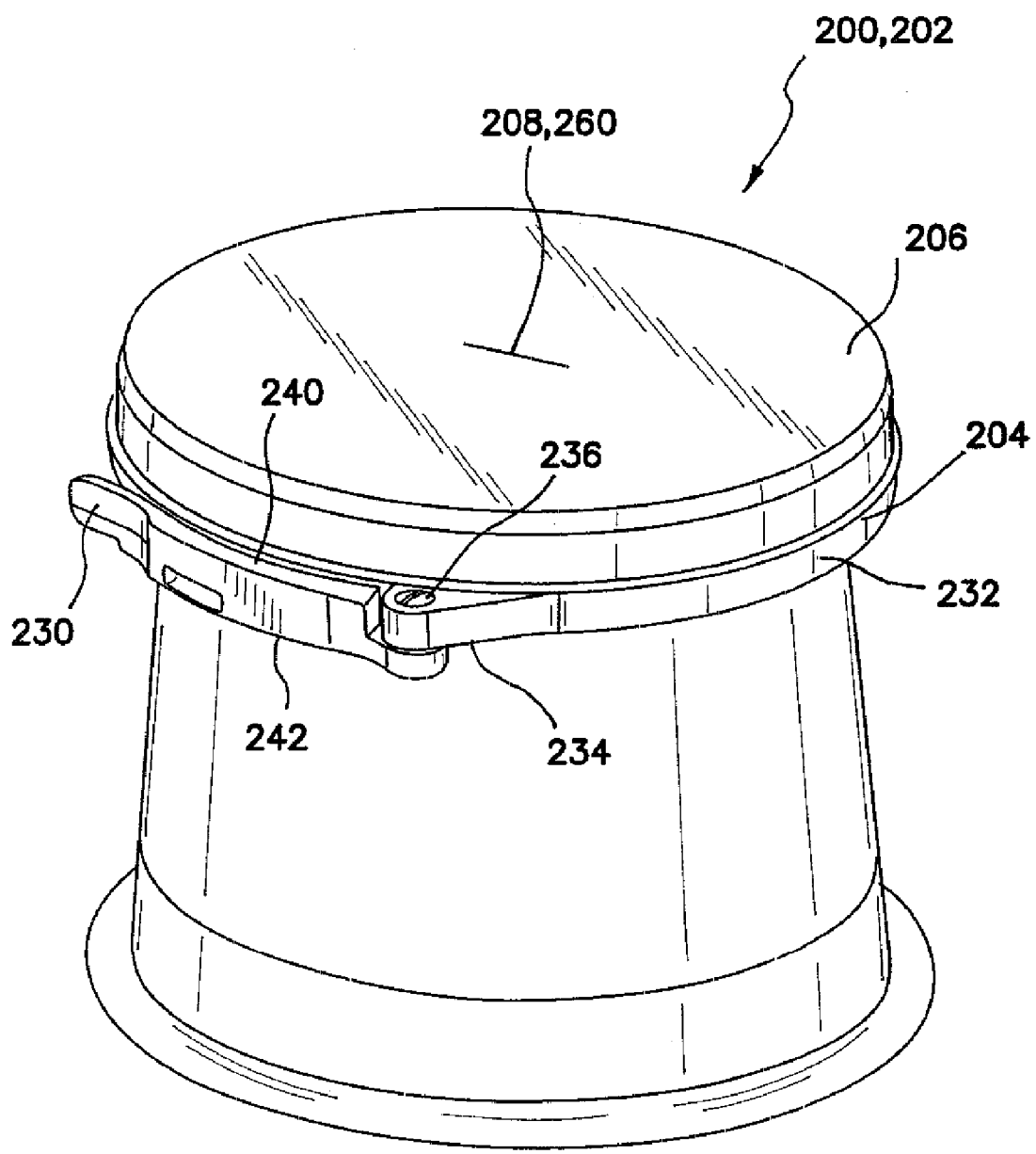
FIG. 23 is a top perspective view of the gel cap of FIG. 16 coupled to the wound retractor.
Figure 24:
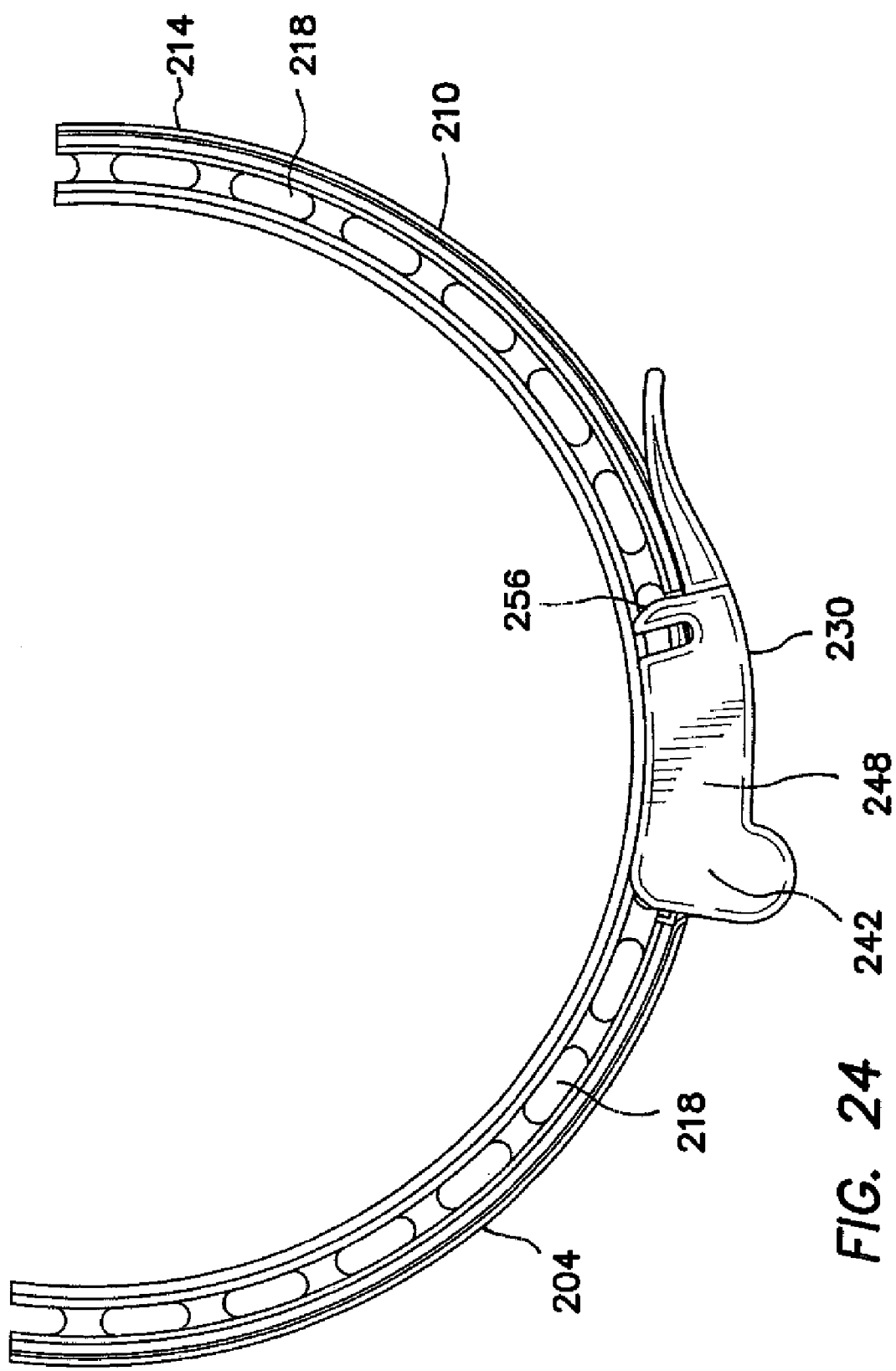
FIG. 24 is a partial bottom view of the cap ring of FIG. 16 with the lever in the second, closed state.
Figure 25:
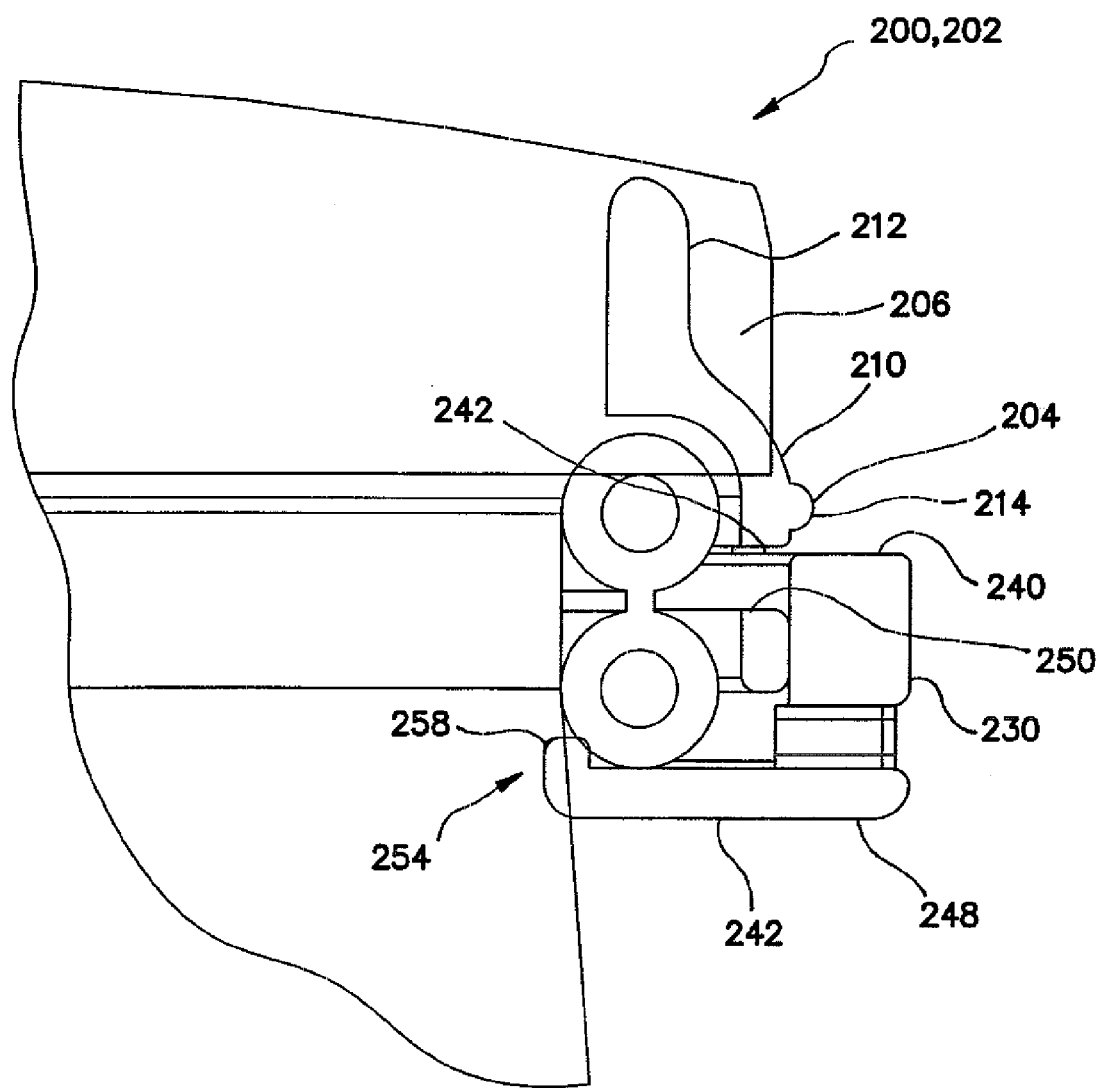
FIG. 25 is a partial section view of the gel cap of FIG. 16 coupled to the outer ring of the wound retractor with the lever in a second, closed state and the lever having a catch for engaging the outer ring of the wound retractor to hold the lever in the closed state.

In use, the wound retractor 100 is first used to retract the incision in the body wall of a patient, as described above. With the lever 230 in the first state, the gel cap 202 is brought to the outer ring 102 of the wound retractor 100 at an angle with the lip portion 224 of the cap ring 204 toward the patient. The lip portion 224 of the cap ring is slid under the distal-most circular tube 108, 110 of the outer ring 102, between the outer ring and the patient, and then the remainder of the gel cap 202 is swung onto the outer ring. The lever 230 is then swung closed into the second state (FIG. 23). In the second state, the distal lip 244 of the lever 230 abuts the distal surface of the distal-most circular tube 108, 110 of the outer ring 102 of the wound retractor 100 and secures the gel cap 202 to the wound retractor. More particularly, with the gel cap 202 mounted onto the outer ring 102 of the wound retractor 100 and the lever 230 positioned in the second state, the lip portion 224 of the cap ring 204 and the distal lip 244 of the lever receive the outer ring of the wound retractor. The outer ring 102 of the wound retractor 100 is positioned between the lip portion 224 of the cap ring 204 and the distal lip 244 of the lever 230 at the distal end of the outer ring of the wound retractor and the gel pad 206 at the proximal end of the outer ring of the wound retractor.

The lever 230 includes locking means 254 (FIG. 20) to prevent unintended opening of the lever from the second state to the first state. In one aspect, to positively lock the lever 230 into the second state, one of the distal and proximal lips 244, 248 of the lever includes a latch 256 that engages the groove/aperture 250, 252 in the cap ring through which the lip protrudes (see FIG. 24). In another aspect, the distal lip 244 of the lever 230 includes a catch 258 (FIG. 25) protruding proximally to engage the distal-most circular tube 108, 110 of the outer ring 102 of the wound retractor 100 at a position on the inner circumference of the outer ring.

With the gel cap 202 mounted onto the outer ring 102 of the wound retractor 100 and the lever 230 positioned in the second state, the proximal lip 248 on the lever positioned in the aperture 252 in the cap ring 204 provides support for the lever to counteract cantilever forces induced by the displaced gel of the gel pad 206. Support of the proximal lip 248 also helps the distal lip 244 maintain the position of the outer ring 102 of the wound retractor 100 against the gel pad 206.

In another aspect, the gel cap 202 may include more than one lever 230 with the levers substantially equally spaced between each other and the lip 224 on the cap ring 204. In a further aspect, the lip 224 on the cap ring 204 may be omitted and at least two levers 230 used to secure the gel cap 202 to the wound retractor 100. The two levers 230 may be substantially diametrically opposed about the circumference of the distal portion of the cap ring.

The gel cap 202 with the lip 224 and lever 230 on the cap ring is best suited for use with wound retractors 100 having an outer ring 102 that is substantially rigid and noncompliant. If the outer ring 102 of the wound retractor 100 were not rigid, the outer ring would tend to pull out of the gel cap 202, thereby compromising the seal between the gel pad 206 and the wound retractor and potentially resulting in deflation of the insufflated body cavity.

The cap ring 204 in one aspect includes a polymer, e.g., polyethylene (PE). In one aspect, the polyethylene is a low density polyethylene (LDPE) or high density polyethylene (HDPE), or ultra high molecular weight polyethylene (UHMWPE). In one aspect, the cap ring 204 may be made of a polymer, such as polycarbonate and may be fabricated by methods including injection molding.

The gel pad 206 may be coupled to, attached to, formed or integrated with the cap ring 204 so that a gas-tight conduit is formed between the cap ring and the sleeve 106. The gel pad 206 covers and seals the entire opening in the cap ring 204. Additionally, the gel pad 206 is adapted to cover substantially the entire wound 400 opening. As stated above, in one aspect the gel pad includes a plurality of intersecting dead-end slits 260, 262 that form an access portion or passage through the gel pad 206. Unlike foam rubber or other similar types of elastic materials, the gel pad 206 provides a gas tight seal around a variety of shapes and sizes of hands or instruments inserted therethrough.

In one aspect, the gel material from which the gel pad 206 is made is an elastomeric gel. Some such gels have been described in U.S. patent application Ser. No. 10/381,220, filed Mar. 20, 2003, the disclosure of which is hereby incorporated by reference as if set forth in full herein. The gel can be prepared by mixing a triblock copolymer with a solvent for the midblocks. The endblocks are typically thermoplastic materials, such as styrene, and the midblocks are thermoset elastomers such as, isoprene or butadiene, e.g. Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and, by the nature of the endblocks, processable as thermoplastic elastomers henceforward. The mixture or slurry has a minimum temperature at which it becomes a gel, i.e., the minimum gelling temperature (MGT). This temperature, in one aspect, corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependant on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a seventy percent (70%) SEB thirty percent (30%) SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include PVC, Isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing bonding sites or a surface charge. Additionally, oil based colorants may be added to the slurry to create gels of different colors.

In one aspect, the mixture/slurry used with the various embodiments of the cap rings that are described herein are composed of about ninety percent (90%) by weight of mineral oil and about ten percent (10%) by weight of KRATON G1651. From a thermodynamic standpoint, this mixture behaves similar to mineral oil. Mineral oil has a considerable heat capacity and, therefore, at about 130° C. it can take three (3) or four (4) hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect, the gel may be air-cooled. Those familiar with the art will recognize that other cooling techniques that are well known in the art may be employed and are contemplated as within the scope of the present invention.

Many of the properties of the KRATON/oil mixture will vary with adjustments in the weight ratio of the components. In general, the greater the percentage of mineral oil the less firm the mixture; the greater the percentage of KRATON, the more firm the mixture. If the resultant gel is too soft it can lead to excessive tenting or doming of the gel cap during surgery when a patient's abdominal cavity is insufflated. Excessive tenting or doming may cause the slits 260, 262 to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about one (1.0) atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about ten percent (10%). Degassing the slurry helps reduce the potential of the finished gel to oxidize.

Degassing the slurry tends to make the resultant gel firmer. A degassed slurry composed of about 91.6% by weight of mineral oil and about 8.4% by weight of KRATON G1651, an eleven-to-one ratio, results in a gel having about the same firmness as a gel made from a slurry that is not degassed and that is composed of about ninety percent (90%) by weight of mineral oil and about ten percent (10%) by weight of KRATON G1651, a nine-to-one ratio.

Mineral oil is of a lighter density than KRATON and the two components will separate after mixing, with the lighter mineral oil rising to the top of the container. This separation may occur when attempting to form static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

The gel pad or gel cap in various aspects of the present invention may be gamma sterilized. The relative or comparative simplicity of qualifying the sterilization process, for example of gamma versus ethylene oxide, of the gel pad and the device with the gel pad is desirable. However, under gamma sterilization large bubbles can form in the gel pad causing potential cosmetic or aesthetic issues in the sterilized devices. The bubbles are more than ninety-nine percent (99%) room air, so removal of the dissolved air in the slurry is performed prior to forming the slurry into gel. For example, the slurry may be degassed via vacuum, as described above, and turned into gel by heat. Bubbles may still form in the gel during gamma sterilization but disappear in a period of about twenty-four (24) to seventy-two (72) hours. In one aspect, the percentage of dissolved gas in the mineral oil at room temperature is about ten percent (10%). The removal of the air in the gel has an additional effect of making the gel firmer. This however is counterbalanced by the softening effect on the gel caused by gamma radiation during gamma sterilization.

If the gel pad is to be gamma sterilized, the gel may include about ninety percent (90%) mineral oil by weight and about ten percent (10%) KRATON by weight. As stated above, degassing the slurry has the effect of making the gel firmer. However, the gamma radiation softens the gel to substantially the same firmness as a gel having about ninety percent (90%) mineral oil by weight and about ten percent (10%) KRATON by weight that is not degassed and gamma sterilized.

In one aspect, cyanoacrylate, e.g., SUPERGLUE or KRAZY GLUE, may be used to bond or otherwise couple or attach the gel pad 206 to the cap ring 204. The glue may attach to either the rubber or styrene component of the tri-block and the bond is frequently stronger than the gel material itself. In another aspect, a solvent may be used to dissolve the plastics in the cap ring and the polystyrene in the gel pad. The solution of solvent is applied to the gel pad and cap ring in either a spray or dip form. In effect, the solution melts both the plastic of the cap ring as well as the polystyrene in the gel pad to allow a chemical bond to form between the two, which remains when the solvent evaporates.

Polyethylene can be dissolved in mineral oil and then applied to the gel pad. The mineral oil will not evaporate but will over time absorb into the gel pad and impart a polyethylene layer on the gel pad that may have some beneficial properties.

In one aspect, the gel pad 206 is cast into a DYNAFLEX or KRATON polymer support structure, e.g., the cap ring 204. By using KRATON polymer or a similar material in the cap ring, ring adhesion between the gel pad 206 and the cap ring 204 can be achieved. The polystyrene in the gel pad 206 is identified as achieving adhesion with polyphenylene oxide (PPO), polystyrene and other polymers.

In the casting process the gel pad 206 and the cap ring 204 are heated to a temperature above about 130° C. and held at that temperature for several hours, e.g., about three (3) to four (4) hours. The temperature used is not sufficient to deform the cap ring 204.

As stated above, in one aspect the cap ring 204 includes a polymer, e.g., polyethylene (PE). The gel includes mineral oil. PE has a higher molecular weight than mineral oil. PE is dissolved by mineral oil at high temperatures. As such, as the PE and the mineral oil in the gel pad 206 intermix as both are heated to and held at temperatures above about 130° C., a bond between the PE and gel pad is formed.

In one aspect, the cap ring 204 includes polycarbonate. The polycarbonate of the cap ring 204 does not form bonds with the gel pad 206 at 130° C. However, by raising the temperature to about 150° C. for a few minutes during casting, bonding occurs between the gel pad 206 and the cap ring 204. As such, heating the gel pad 206 and cap ring 204 to temperatures at which both the polystyrene of the gel and the polycarbonate are simultaneously beyond their melt points allow bonds to form between the gel pad and the cap ring. Alternatively, the gel pad 206 and cap ring 204 may be heated to near or at the glass transition temperature of the polycarbonate cap ring to form the bond between the gel pad and the cap ring.

In one aspect, casting the gel pad 206 into the cap ring 204 to form a gel cap 202 includes placing the cap ring into a mold cavity of a casting mold. The mold cavity may include support for the annular walls of the cap ring 204. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention as well.

The mold cavity having the cap ring 204 is filled with the slurry such that the slurry is in contact with the cap ring. To facilitate filling voids in the mold cavity with the slurry, the slurry may be preheated, for example, to about 52° C. (125° F.). Preheating the slurry to a temperature below the MGT reduces the viscosity of the slurry and allows the slurry to flow more easily. As stated above, the slurry may have been degassed in a vacuum. The slurry may be degassed again within the mold after the mold cavity is filled to remove air that may have been introduced during the filling of the mold cavity and to facilitate flow of the slurry into voids in the mold. Heat is applied to the mold having the cap ring 204 and the slurry, such as in an oven, until the slurry attains a temperature of about 150° C. As stated above, the slurry turns into gel at about 120° C., however, at about 150° C., the gel can bond to a polycarbonate cap ring 204. Depending on the material used to fabricate the cap ring 204, bonding may take place at temperatures other than about 150° C. If the cap ring 204 is fabricated of a material having a lower melting point than 120° C., then the gel pad 206, such as a gel slug 206, may be molded separately and then bonded to the cap ring. The slits 260, 262 may be molded into the gel pad 206 through the use of an insert in the form of the slit in the mold.

Once the temperature of the gel pad 206 reaches about 150° C., the gel cap 202 may be cooled, such as by air-cooling, cold-water immersion, or other cooling means that are well known in the art. At 150° C. the gel pad is soft and if it were distorted during cooling it would set with the distortion included. To reduce the likelihood of distorting the gel pad 206, the gel cap 202 may be cooled within the mold. Cooling times may vary based on parameters including size and configuration of the mold, quantity of gel, temperature and quantity of cooling medium, cooling medium properties and the mold material. As an example, the cooling time may be about two (2) hours if cooling in air and about fifteen (15) minutes if cooling in water. Whether cooling with air or water, the final properties of the gel are substantially the same. The gel cap 202 is typically cooled to about ambient room temperature, but may be cooled to lower temperatures. If the gel cap 202 is cooled to the freezing point of the gel, about 0° C., then the gel will freeze and become hard. This may be beneficial for other means of coupling the gel pad 206 to the cap ring 204, such as with a secondary operation. The gel cap 202 may be removed from the mold at any time after the gel has set.

When removed from the mold, the gel pad 206 typically has a tacky surface. The gel cap 202 may be coated with a powder, such as cornstarch, to substantially reduce or eliminate the tackiness of the cured gel pad 206.

As stated above, in another aspect, the gel pad 206 may be molded separately from the cap ring 204 and coupled to the cap ring by a secondary operation, such as by bonding. In one aspect, the gel pad 206 may be molded into a gel slug 206 having an outer perimeter smaller than the inner cylindrical wall of the cap ring 204 and to a height higher that the height of the cap ring. Since the gel pad 206 is being molded separate from the cap ring 204, the slurry only needs to be heated until it reaches about 120° C. and completes the transformation from slurry into gel and the gel becomes substantially transparent. The gel slug 206 may then be placed within the inner cylindrical wall of the cap ring 204. The gel slug 206 may be cooled and/or frozen prior to placing it within the inner cylindrical wall of the cap ring 204. The gel slug 206 may be coupled to the cap ring 204 through compression molding with the gel slug being compressed longitudinally so that the outer perimeter of the gel slug expands and compresses against the inner cylindrical wall of the cap ring. The gel slug 206 and cap ring 204 are heated to a sufficient temperature for the polystyrene of the gel and the polymer of the cap ring to form bonds between the gel and the cap ring. Molding the gel slug 206 separately from the cap ring 204 and heat bonding the gel slug to the cap ring at a later time is especially useful when the cap ring is made of a material that has a lower melting temperature than the MGT. In such situations, the gel slug 206 can be molded first and heat bonded to the cap ring 204 without melting the cap ring.

An advantage associated with the modified surgical access device is it enables a surgeon to quickly retract and protectively line an abdominal wall incision while being able to easily accommodate variations in abdominal wall thickness between patients. In addition, the device effectively seals around the interior and exterior of the incision, and allows a sealing cap to be coupled to the device to seal the abdominal cavity and to enable a laparoscopic procedure to be performed.

Many alterations and modifications may be made by those having ordinary skill in the art without departing from the spirit and scope of the invention. For these reasons, the above description should not be construed as limiting the invention, but should be interpreted as merely exemplary of the embodiments.

The invention claimed is:
1. A surgical access device, comprising:
a wound retractor for retracting an opening in a biological body wall, the wound retractor having,
an outer ring having an annular axis and adapted for juxtaposition with an outer surface of the biological body wall,
an inner ring adapted for juxtaposition with an inner surface of the biological body wall, and
a sleeve coupling the outer ring to the inner ring, the sleeve being adapted to traverse the opening in the body wall,
wherein the outer ring has a neutral state, in which the outer ring is substantially noncompliant, and a transitional state, in which the outer ring is rolled over itself around the annular axis, thereby rolling the sleeve around the outer ring to retract and seal the opening in the body wall; and a gel cap adapted for direct attachment to the outer ring of the wound retractor in the neutral state, the gel cap having,
- a cap ring adapted to be coupled to the outer ring of the wound retractor,
- a lip disposed at a distal end of the cap ring, the lip curving radially inward from a wall of the cap ring and extending around a portion of a circumference thereof,
- a lever spaced from the lip of the cap ring and pivotably coupled to the cap ring, the lever pivoting on a plane that is perpendicular to a longitudinal axis of the cap ring, the lever comprising a flat, distal lip positioned at a distal end of the lever and lying in a plane that is positioned perpendicular to the longitudinal axis of the cap ring, and
- a gel pad coupled to the cap ring, the gel pad being made of a gel material, the gel pad including an access portion for providing a passage from external the body to a body cavity, the passage forming an instrument seal in the presence of an instrument inserted therethrough and a zero seal in the absence of an instrument inserted therethrough, wherein
- in an open state, the lever is pivoted outwardly, away from a body of the cap ring, and
- in a closed state, with the outer ring of the wound retractor positioned within the cap ring, the lever is pivoted toward the cap ring such that the distal lip of the lever protrudes radially inwardly from the body of the cap ring, and the lip of the cap ring and the distal lip of the lever abut the distal surface of the outer ring of the wound retractor, thereby securing the gel cap to the wound retractor.

2. The surgical access device of claim 1, the outer ring of the wound retractor having a lumen, and further comprising:
a substantially noncompliant hoop positioned in the lumen of the outer ring of the wound retractor.

3. The surgical access device of claim 2, the outer ring of the wound retractor having two lumens, and further comprising:
a substantially noncompliant hoop positioned in each of the two lumens of the outer ring of the wound retractor.

4. The surgical access device of claim 1, the sleeve including a material that is flexible and impermeable to fluids and bacteria.

5. The surgical access device of claim 1, the inner ring being made of materials having sufficient hardness to retain the shape of the inner ring after insertion of the inner ring into a body cavity.

6. The surgical access device of claim 1, the outer ring being made of materials that allow the outer ring to be turned around its annular axis.

7. The surgical access device of claim 1, wherein the lip of the cap ring and the lip of the lever being configured to receive the outer ring of the wound retractor such that the outer ring of the wound retractor is positioned between the lip of the cap ring and the lip of the lever at a distal end and the gel pad at a proximal end.

8. The surgical access device of claim 1, wherein a distal portion of the cap ring is adapted to receive the outer ring of the wound retractor such that the outer ring of the wound retractor embeds into the gel pad and displaces the gel, thereby forming a seal between the gel pad and the outer ring and sleeve of the wound retractor.

9. The surgical access device of claim 1, the access portion of the gel pad including a plurality of intersecting dead-end slits.

10. The surgical access device of claim 1, wherein the gel pad covers and seals the entire opening in the cap ring.

11. The surgical access device of claim 1, wherein the gel pad is adapted to cover the entire surgical opening.

12. The surgical access device of claim 1, the outer surface of the cap ring including a lug, the lever being coupled to the lug.

13. The surgical access device of claim 1, the lever including locking means for facilitating prevention of unintended opening of the lever from the second state to the first state.

14. The surgical access device of claim 1, the gel cap including more than one lever with the levers being equally spaced between each other and the lip on the cap ring.

15. The surgical access device of claim 1, wherein the lever is substantially opposite the lip on the cap ring.

16. A surgical access device, comprising:
a wound retractor for retracting an opening in a biological body wall, the wound retractor having
- an outer ring having an annular axis and adapted to be positioned near a proximal surface of the biological body wall,
- an inner ring adapted to be positioned near a distal surface of the biological body wall, and
- a sleeve coupling the outer ring to the inner ring,
- wherein the outer ring has a neutral state, in which the outer ring is substantially noncompliant, and a transitional state, in which the outer ring is rolling over itself around the annular axis, thereby rolling the sleeve around the outer ring to retract and seal the opening in the body wall; and a gel cap adapted for being attached to the outer ring of the wound retractor in the neutral state, the gel cap having
- a cap ring adapted to be coupled to the outer ring of the wound retractor,
- a lever pivotably coupled to the cap ring, and
- a gel pad coupled to the cap ring and including an access portion for providing a passage from external the body to a body cavity, the passage forming an instrument seal in the presence of an instrument inserted therethrough and a zero seal in the absence of an instrument inserted therethrough,
- wherein the outer ring of the wound retractor is configured to be positioned within the cap ring such that pivoting the lever relative to the cap ring secures the gel cap to the wound retractor.

17. A surgical access device, comprising:
a wound retractor for retracting an opening in a biological body wall, the wound retractor comprising:
- an outer ring having an annular axis and adapted to be positioned proximally of a proximal surface of the biological body wall,
- an inner ring adapted to be positioned distally of a distal surface of the biological body wall, and
- a sleeve coupling the outer ring to the inner ring,
- wherein the outer ring has a neutral state, in which the outer ring is substantially noncompliant, and a transitional state, in which the outer ring is rolling over itself around the annular axis, thereby rolling the sleeve around the outer ring to retract and seal the opening in the body wall; and a sealing cap adapted for being coupled to the outer ring of the wound retractor in the neutral state.

18. The surgical access device of claim 17, wherein the sealing cap comprises a gel seal including an access portion for providing a passage from external the body to a body cavity, the passage forming an instrument seal in the presence of an instrument inserted therethrough and a zero seal in the absence of an instrument inserted therethrough.

19. The surgical access device of claim 17, wherein the sealing cap comprises a lever.

20. The surgical access device of claim 17, further comprising a wound retractor having an outer ring, an inner ring, and a sleeve, wherein the outer ring has a neutral state in which the outer ring is substantially noncompliant and a transitional state in which the outer ring is rolling over itself around the annular axis thereby rolling a sleeve around the outer ring to retract and seal an opening in a body wall.

21. A surgical access device, comprising:
  a wound retractor for retracting an opening in a biological body wall, the wound retractor comprising:
    an outer ring having an annular axis and adapted to be positioned proximally of a proximal surface of the biological body wall,
    an inner ring adapted to be positioned distally of a distal surface of the biological body wall, and
    a sleeve coupling the outer ring to the inner ring,
  wherein the outer ring has a neutral state, in which the outer ring is substantially noncompliant, and a transitional state, in which the outer ring is rolling over itself around the annular axis, thereby rolling the sleeve around the outer ring to retract and seal the opening in the body wall.

22. The surgical access device of claim 21, the outer ring of the wound retractor having a lumen, and further comprising:
  a substantially noncompliant hoop positioned in the lumen of the outer ring of the wound retractor.

23. The surgical access device of claim 22, the outer ring of the wound retractor having two lumens, and further comprising:
  a substantially noncompliant hoop positioned in each of the two lumens of the outer ring of the wound retractor.

24. The surgical access device of claim 23, further comprising a sealing cap adapted for being coupled to the outer ring of the wound retractor in the neutral state.

25. The surgical access device of claim 24, wherein the sealing cap comprises a gel seal.

26. A surgical access device, comprising:
  a gel cap adapted for being attached to an outer ring of a wound retractor having a neutral state in which the outer ring is substantially noncompliant and a transitional state in which the outer ring is rolling over itself around an annular axis thereby rolling a sleeve around the outer ring to retract and seal an opening in a body wall, the gel cap comprising
    a cap ring adapted to be coupled to the outer ring of the wound retractor, and
    a gel pad coupled to the cap ring and including an access portion for providing a passage from external the body to a body cavity, the passage forming an instrument seal in the presence of an instrument inserted therethrough and a zero seal in the absence of an instrument inserted therethrough,
  wherein the gel cap further comprises a lever pivotably coupled to the cap ring, and wherein the cap ring is configured to be positioned around the outer ring of the wound retractor such that pivoting the lever relative to the cap ring secures the gel cap to the wound retractor.

\* \* \* \* \*